(12) United States Patent
Kostrzewski et al.

(10) Patent No.: US 10,582,927 B2
(45) Date of Patent: Mar. 10, 2020

(54) SURGICAL APPARATUS

(71) Applicant: Covidien LP, Mansfield, MA (US)

(72) Inventors: Stanislaw Kostrzewski, Newtown, CT (US); Ernest Aranyi, Easton, CT (US)

(73) Assignee: Covidien LP, Mansfield, MA (US)

( * ) Notice: Subject to any disclaimer, the term of this patent is extended or adjusted under 35 U.S.C. 154(b) by 273 days.

(21) Appl. No.: 15/625,395

(22) Filed: Jun. 16, 2017

(65) Prior Publication Data
US 2017/0281156 A1 Oct. 5, 2017

Related U.S. Application Data

(63) Continuation of application No. 14/166,366, filed on Jan. 28, 2014, now Pat. No. 9,700,312.

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 2017/00473* (2013.01);
(Continued)

(58) Field of Classification Search
CPC ............ A61B 17/068; A61B 17/07207; A61B 2017/00473; A61B 2017/00477;
(Continued)

(56) References Cited

U.S. PATENT DOCUMENTS 2,887,111 A    5/1959  Diaz
4,545,373 A   10/1985  Christoudias
(Continued)

FOREIGN PATENT DOCUMENTS

CA    2185154 C    9/2006
EP    1785102 A2   5/2007
(Continued)

OTHER PUBLICATIONS

Japanese Notice of Allowance dated Feb. 5, 2019 issued in corresponding JP Appln. No. 2014-260013 (Summary only).
(Continued)

*Primary Examiner* — Gloria R Weeks
*Assistant Examiner* — Dariush Seif
(74) *Attorney, Agent, or Firm* — Carter, DeLuca & Farrell LLP

(57) ABSTRACT

A surgical stapling apparatus includes an actuating device including an elongated shaft. A tool assembly is disposed on a distal end of the shaft. The tool assembly includes a first jaw member supporting a cartridge assembly having a plurality of surgical fasteners, and a second jaw member supporting an anvil. The first jaw member is movable in relation to the second jaw member between a spaced position and an approximated position. One of the first or second jaw members includes a cantilever at a proximal end thereof. A firing cam bar assembly is slidably disposed within the tool assembly and includes a cam surface configured to engage the cantilever to move the first and second jaw member towards the approximated position and a distal end configured to deploy the plurality of surgical fasteners from the cartridge assembly.

16 Claims, 28 Drawing Sheets

(51) Int. Cl.
*A61B 17/00* (2006.01)
*A61B 17/29* (2006.01)

(52) U.S. Cl.
CPC ........... *A61B 2017/00477* (2013.01); *A61B 2017/07228* (2013.01); *A61B 2017/07278* (2013.01); *A61B 2017/07285* (2013.01); *A61B 2017/2932* (2013.01); *A61B 2017/2933* (2013.01)

(58) Field of Classification Search
CPC ........... A61B 2017/07278; A61B 2017/07285; A61B 2017/2932; A61B 2017/2933
USPC .............. 227/175.1–182.1; 606/75, 219, 220
See application file for complete search history.

(56) References Cited

U.S. PATENT DOCUMENTS

| | | |
|---|---|---|
| 4,576,164 A | 3/1986 | Richeson |
| 4,601,710 A | 7/1986 | Moll |
| 4,723,545 A | 2/1988 | Nixon et al. |
| 4,873,977 A | 10/1989 | Avant et al. |
| 5,047,039 A | 9/1991 | Avant et al. |
| 5,129,570 A | 7/1992 | Schulze et al. |
| 5,217,460 A | 6/1993 | Knoepfler |
| 5,234,454 A | 8/1993 | Bangs |
| 5,281,236 A | 1/1994 | Bagnato et al. |
| 5,282,807 A | 2/1994 | Knoepfler |
| 5,350,104 A | 9/1994 | Main et al. |
| 5,355,897 A | 10/1994 | Pietrafitta et al. |
| 5,360,154 A | 11/1994 | Green |
| 5,376,376 A | 12/1994 | Li |
| 5,397,324 A | 3/1995 | Carroll et al. |
| 5,425,745 A | 6/1995 | Green et al. |
| 5,445,644 A | 8/1995 | Pietrafitta et al. |
| 5,447,265 A * | 9/1995 | Vidal ............... A61B 17/07207 227/176.1 |
| 5,467,911 A | 11/1995 | Tsuruta et al. |
| 5,487,500 A | 1/1996 | Knodel et al. |
| 5,501,654 A | 3/1996 | Failla et al. |
| 5,507,754 A | 4/1996 | Green et al. |
| 5,507,773 A * | 4/1996 | Huitema .......... A61B 17/07207 600/564 |
| 5,522,788 A | 6/1996 | Kuzmak |
| 5,527,298 A | 6/1996 | Vance et al. |
| 5,531,744 A | 7/1996 | Nardella et al. |
| 5,562,241 A * | 10/1996 | Knodel ............ A61B 17/07207 227/175.1 |
| 5,597,107 A | 1/1997 | Knodel et al. |
| 5,603,698 A | 2/1997 | Roberts et al. |
| 5,632,432 A | 5/1997 | Schulze et al. |
| 5,662,258 A | 9/1997 | Knodel et al. |
| 5,665,100 A * | 9/1997 | Yoon ..................... A61B 10/06 606/139 |
| 5,673,841 A | 10/1997 | Schulze et al. |
| 5,690,653 A | 11/1997 | Richardson et al. |
| 5,766,187 A | 6/1998 | Sugarbaker |
| 5,772,099 A | 6/1998 | Gravener |
| 5,810,855 A | 9/1998 | Rayburn et al. |
| 5,816,471 A | 10/1998 | Plyley et al. |
| 5,865,361 A * | 2/1999 | Milliman ......... A61B 17/07207 227/176.1 |
| 5,868,759 A * | 2/1999 | Peyser ............... A61B 17/1285 227/901 |
| 5,902,333 A | 5/1999 | Roberts et al. |
| 5,908,427 A | 6/1999 | McKean et al. |
| 5,954,259 A * | 9/1999 | Viola ............... A61B 17/07207 227/176.1 |
| 5,984,964 A | 11/1999 | Roberts et al. |
| 6,032,849 A * | 3/2000 | Mastri ............. A61B 17/07207 227/176.1 |
| 6,099,537 A | 8/2000 | Sugai et al. |
| 6,099,551 A | 8/2000 | Gabbay |
| 6,117,148 A | 9/2000 | Ravo et al. |
| 6,149,660 A | 11/2000 | Laufer et al. |
| 6,165,183 A | 12/2000 | Kuehn et al. |
| 6,193,129 B1 | 2/2001 | Bittner et al. |
| 6,443,970 B1 | 9/2002 | Schulze et al. |
| 6,458,128 B1 | 10/2002 | Schulze |
| 6,464,702 B2 | 10/2002 | Schulze et al. |
| 6,506,210 B1 | 1/2003 | Kanner |
| 6,530,942 B2 | 3/2003 | Fogarty et al. |
| 6,554,829 B2 | 4/2003 | Schulze et al. |
| 6,582,452 B2 | 6/2003 | Coleman et al. |
| 6,592,581 B2 | 7/2003 | Bowe |
| 6,616,661 B2 | 9/2003 | Wellman et al. |
| 6,616,686 B2 | 9/2003 | Coleman et al. |
| 6,620,161 B2 | 9/2003 | Schulze et al. |
| 6,623,482 B2 | 9/2003 | Pendekanti et al. |
| 6,648,900 B2 | 11/2003 | Fleischman et al. |
| 6,648,901 B2 | 11/2003 | Fleischman et al. |
| 6,652,521 B2 | 11/2003 | Schulze |
| 6,656,193 B2 | 12/2003 | Grant et al. |
| 6,673,084 B1 | 1/2004 | Peterson et al. |
| 6,685,712 B2 | 2/2004 | Cummins et al. |
| 6,695,840 B2 | 2/2004 | Schulze |
| 6,702,828 B2 | 3/2004 | Whayne |
| 6,767,356 B2 | 7/2004 | Kanner et al. |
| 6,773,435 B2 | 8/2004 | Schulze et al. |
| 6,773,439 B2 | 8/2004 | George et al. |
| 6,773,444 B2 | 8/2004 | Messerly |
| 6,790,217 B2 | 9/2004 | Schulze et al. |
| 6,821,273 B2 | 11/2004 | Mollenauer |
| 6,905,057 B2 | 6/2005 | Swayze et al. |
| 6,926,731 B2 | 8/2005 | Coleman et al. |
| 6,939,328 B2 | 9/2005 | Raulerson |
| 6,951,568 B1 | 10/2005 | Chin |
| 6,976,969 B2 | 12/2005 | Messerly |
| 7,041,099 B2 | 5/2006 | Thomas et al. |
| 7,063,699 B2 | 6/2006 | Hess et al. |
| 7,090,686 B2 | 8/2006 | Nobles et al. |
| 7,128,748 B2 | 10/2006 | Mooradian et al. |
| 7,147,138 B2 | 12/2006 | Shelton, IV |
| 7,291,161 B2 * | 11/2007 | Hooven ................ A61B 17/29 606/157 |
| 7,300,444 B1 | 11/2007 | Nielsen et al. |
| 7,364,060 B2 | 4/2008 | Milliman |
| 7,396,356 B2 | 7/2008 | Mollenauer |
| 7,402,172 B2 | 7/2008 | Chin et al. |
| 7,404,508 B2 | 7/2008 | Smith et al. |
| 7,419,080 B2 | 9/2008 | Smith et al. |
| 7,500,979 B2 | 3/2009 | Hueil et al. |
| 7,556,186 B2 | 7/2009 | Milliman |
| 7,669,746 B2 | 3/2010 | Shelton, IV |
| 7,682,367 B2 | 3/2010 | Shah et al. |
| 7,857,187 B2 | 12/2010 | Milliman |
| 7,866,523 B1 | 1/2011 | White et al. |
| 7,934,629 B2 * | 5/2011 | Wixey ............... A61B 17/0686 227/175.1 |
| 8,033,438 B2 | 10/2011 | Scirica |
| 8,066,166 B2 | 11/2011 | Demmy et al. |
| 8,070,036 B1 | 12/2011 | Knodel |
| 8,136,711 B2 | 3/2012 | Beardsley et al. |
| 8,403,195 B2 | 3/2013 | Beardsley et al. |
| 8,403,196 B2 | 3/2013 | Beardsley et al. |
| 2002/0069884 A1 | 6/2002 | Boyd et al. |
| 2002/0074004 A1 | 6/2002 | Boyd et al. |
| 2002/0173809 A1 | 11/2002 | Fleischman et al. |
| 2003/0028178 A1 | 2/2003 | Chin |
| 2003/0144686 A1 | 7/2003 | Martinez et al. |
| 2004/0068278 A1 | 4/2004 | Fleischman et al. |
| 2004/0236326 A1 | 11/2004 | Schulze et al. |
| 2004/0243151 A1 | 12/2004 | Demmy et al. |
| 2005/0022601 A1 | 2/2005 | Blakley |
| 2005/0059996 A1 | 3/2005 | Bauman et al. |
| 2005/0080434 A1 | 4/2005 | Chung et al. |
| 2005/0096670 A1 | 5/2005 | Wellman et al. |
| 2005/0096671 A1 * | 5/2005 | Wellman .......... A61B 17/00008 606/139 |
| 2005/0119669 A1 | 6/2005 | Demmy |
| 2005/0143756 A1 | 6/2005 | Jankowski |
| 2005/0216055 A1 | 9/2005 | Scirica et al. |
| 2005/0216057 A1 | 9/2005 | Coleman et al. |

(56) References Cited

U.S. PATENT DOCUMENTS

| | | |
|---|---|---|
| 2005/0228413 A1 | 10/2005 | Binmoeller et al. |
| 2005/0228446 A1 | 10/2005 | Mooradian et al. |
| 2006/0030877 A1 | 2/2006 | Martinez et al. |
| 2006/0129165 A1 | 6/2006 | Edoga et al. |
| 2006/0151568 A1 | 7/2006 | Weller et al. |
| 2006/0208028 A1 | 9/2006 | Kanner |
| 2006/0229643 A1 | 10/2006 | Nolan et al. |
| 2006/0264986 A1 | 11/2006 | Park et al. |
| 2007/0005084 A1 | 1/2007 | Clague et al. |
| 2007/0021840 A1 | 1/2007 | Lopera |
| 2007/0045379 A1* | 3/2007 | Shelton, IV ..... A61B 17/07207 227/176.1 |
| 2007/0149993 A1 | 6/2007 | Kasahara et al. |
| 2007/0187455 A1 | 8/2007 | Demmy et al. |
| 2007/0221700 A1 | 9/2007 | Ortiz et al. |
| 2007/0221701 A1 | 9/2007 | Ortiz et al. |
| 2008/0243145 A1* | 10/2008 | Whitfield ........... A61B 17/1285 606/143 |
| 2008/0249565 A1 | 10/2008 | Michler et al. |
| 2008/0269793 A1 | 10/2008 | Scirica et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2009/0069806 A1 | 3/2009 | De La Mora Levy et al. |
| 2010/0094315 A1 | 4/2010 | Beardsley et al. |
| 2011/0087259 A1* | 4/2011 | Marczyk .............. A61B 17/072 606/170 |
| 2011/0101065 A1 | 5/2011 | Milliman |
| 2011/0180585 A1* | 7/2011 | Czernik ........... A61B 17/07207 227/176.1 |
| 2011/0290245 A1 | 12/2011 | Cuevas et al. |
| 2014/0263567 A1* | 9/2014 | Williams ......... A61B 17/07207 227/180.1 |
| 2015/0209030 A1* | 7/2015 | Kostrzewski ........ A61B 17/068 227/177.1 |
| 2018/0049741 A1* | 2/2018 | Harris .................... A61B 34/30 |

FOREIGN PATENT DOCUMENTS

| | | |
|---|---|---|
| EP | 2090245 A1 | 8/2009 |
| EP | 2130499 A1 | 12/2009 |
| EP | 2586382 A2 | 5/2013 |
| JP | 08182684 | 7/1996 |
| JP | 2007061628 A | 3/2007 |
| JP | 2007105481 A | 4/2007 |
| JP | 2013056233 A | 3/2013 |
| WO | 0121060 A1 | 3/2001 |
| WO | 0200121 | 1/2002 |
| WO | 03094745 A1 | 11/2003 |
| WO | 2004096057 A2 | 11/2004 |
| WO | 2007147439 A1 | 12/2007 |
| WO | 2012040984 A1 | 4/2012 |
| WO | 2012044551 A1 | 4/2012 |

OTHER PUBLICATIONS

Chinese Office Action dated May 18, 2018 issued in corresponding CN Application No. 2014108444265.
European Search Report for EP10251721.6-2310 date of completion Feb. 18, 2011 (3 pages).
European Search Report EP 14 1909678 dated Jun. 3, 2015.
European Search Report dated May 3, 2017 issued in corresponding European Application No. EP16192621.7-1654.
Japanese Office Action dated Oct. 15, 2018 issued in corresponding JP Appln. No. 2014-260013.
Australian Examination Report dated Nov. 28, 2018 issued in corresponding AU Appln. No. 2014259515.

* cited by examiner

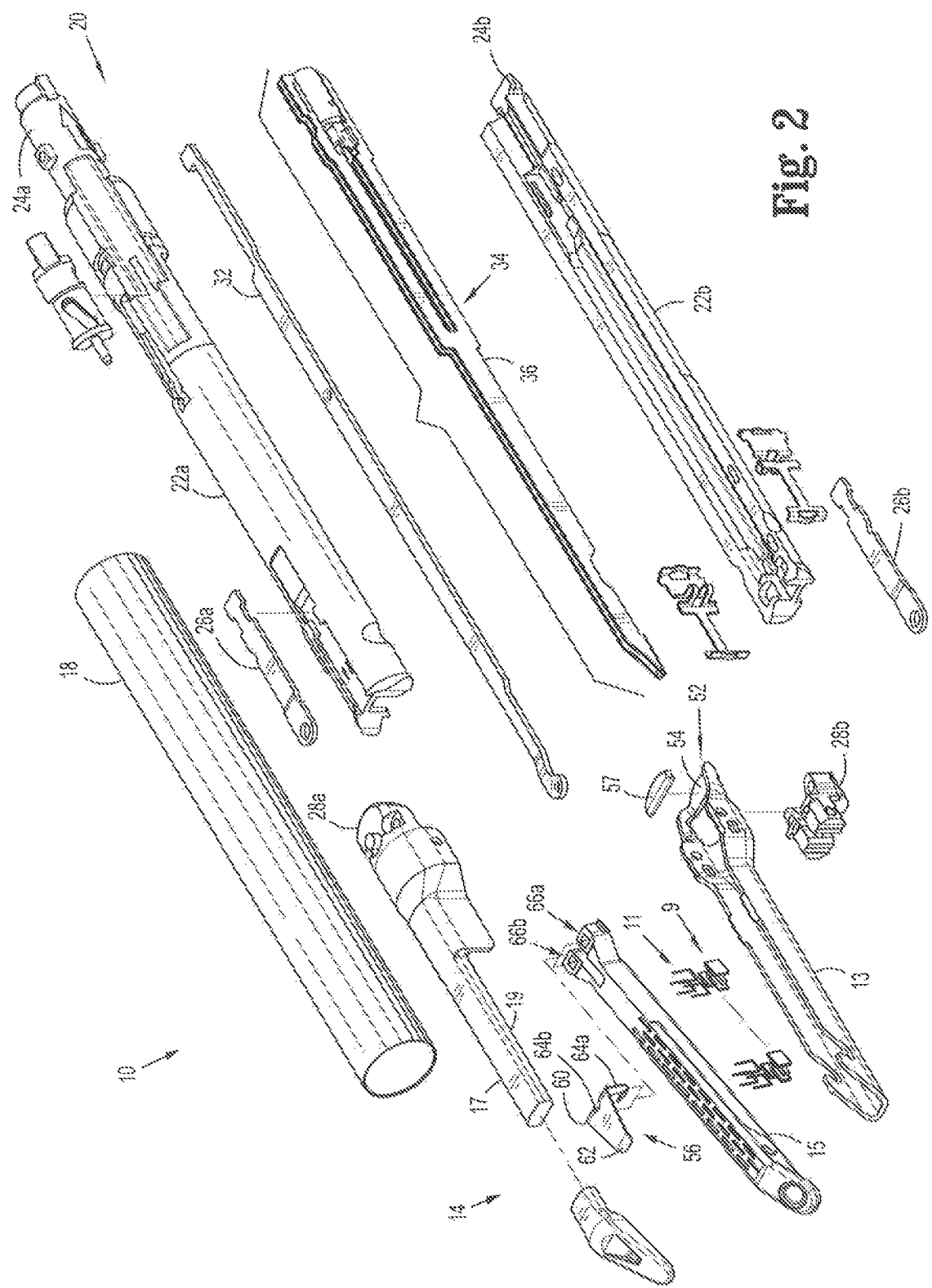

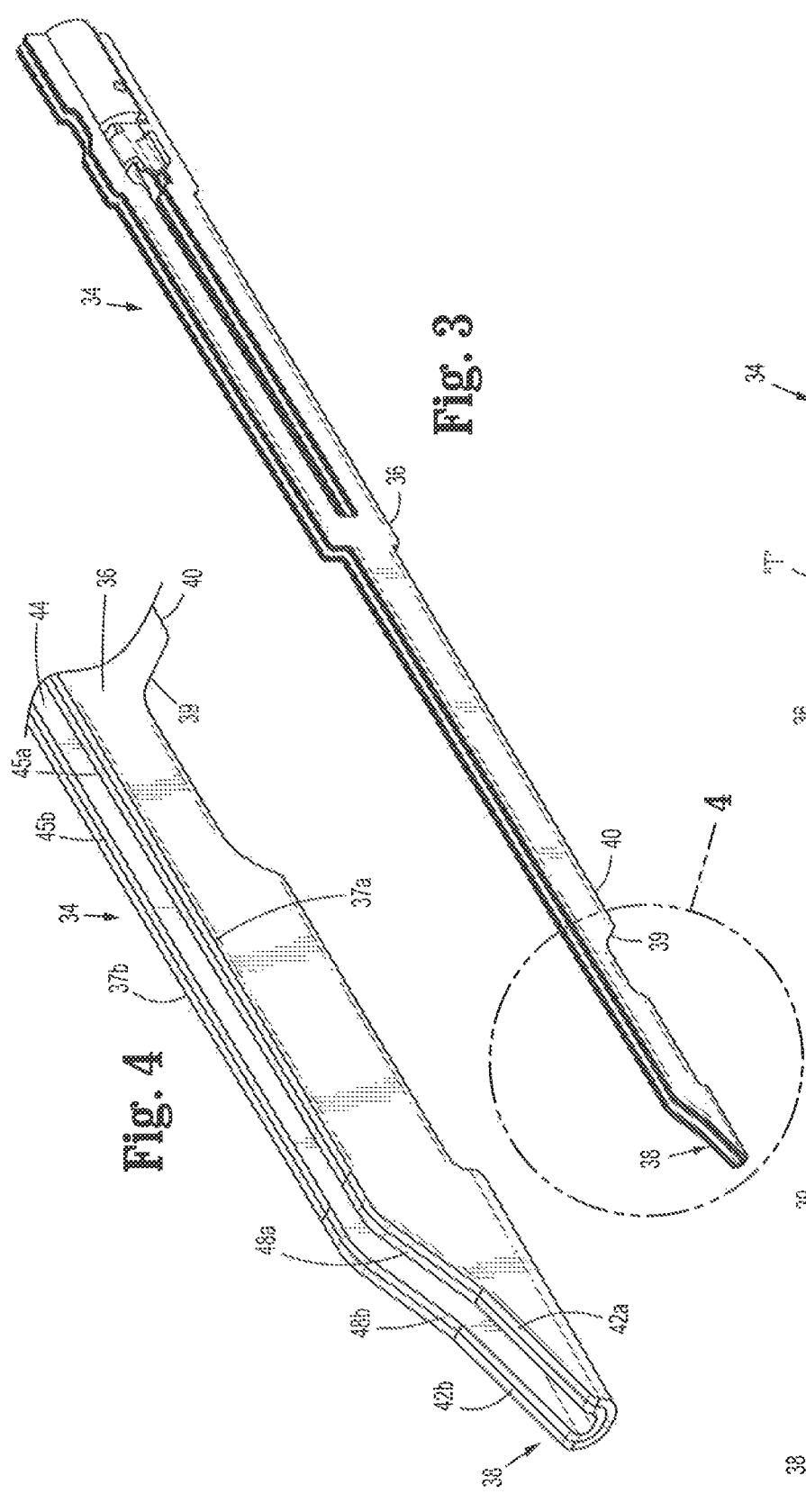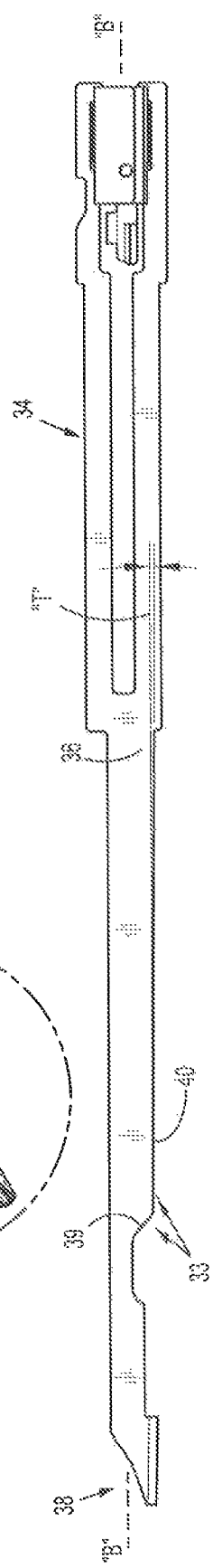

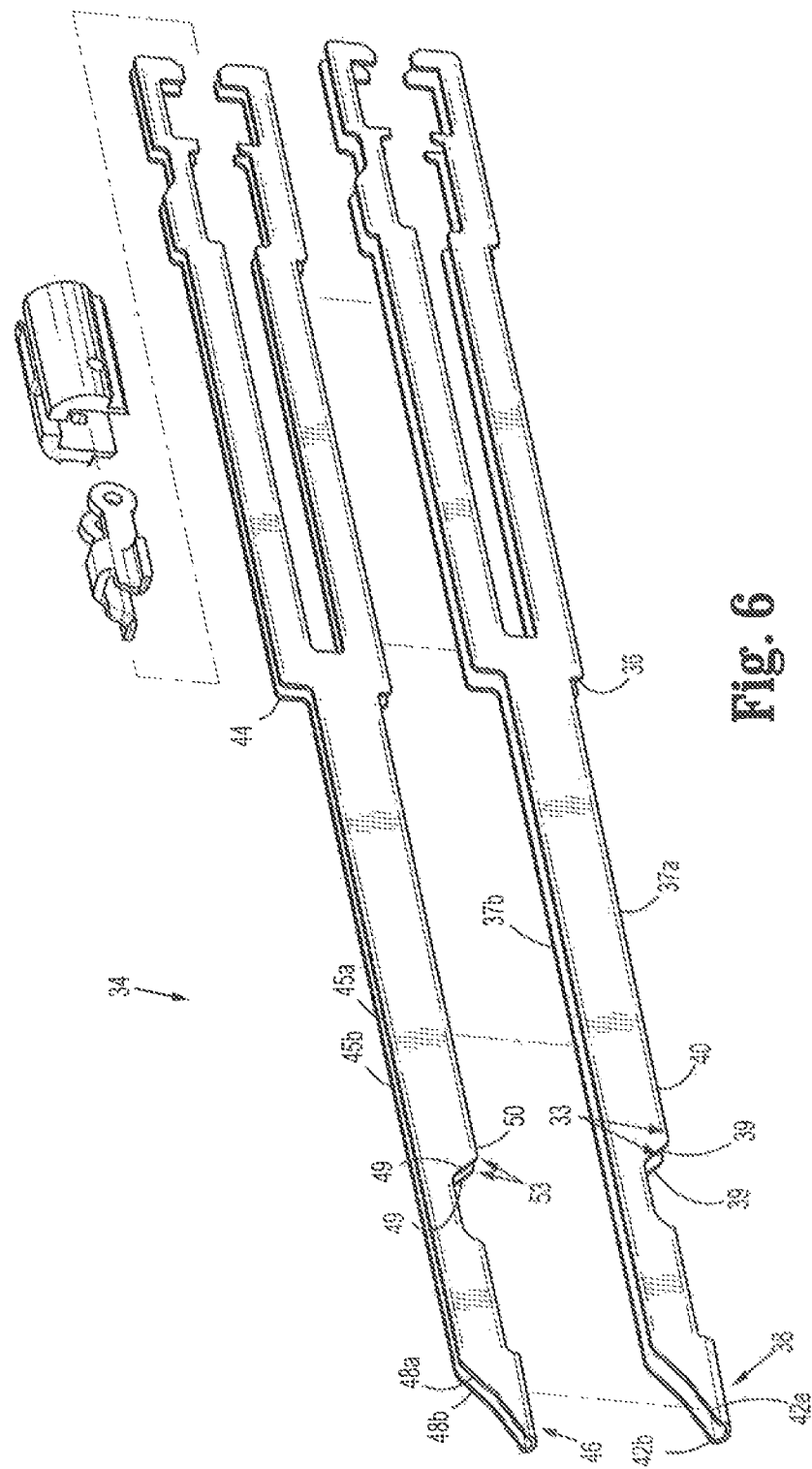

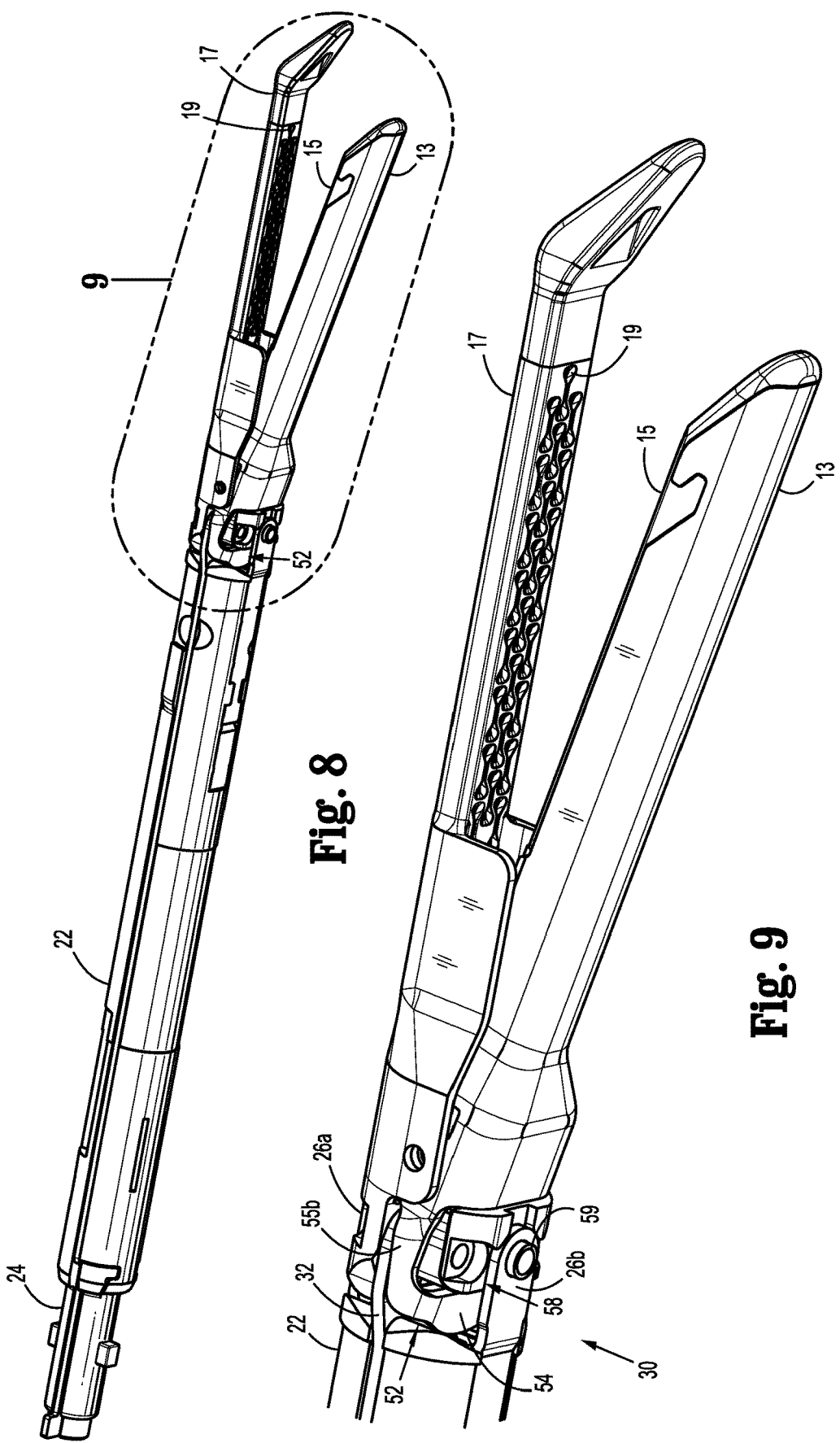

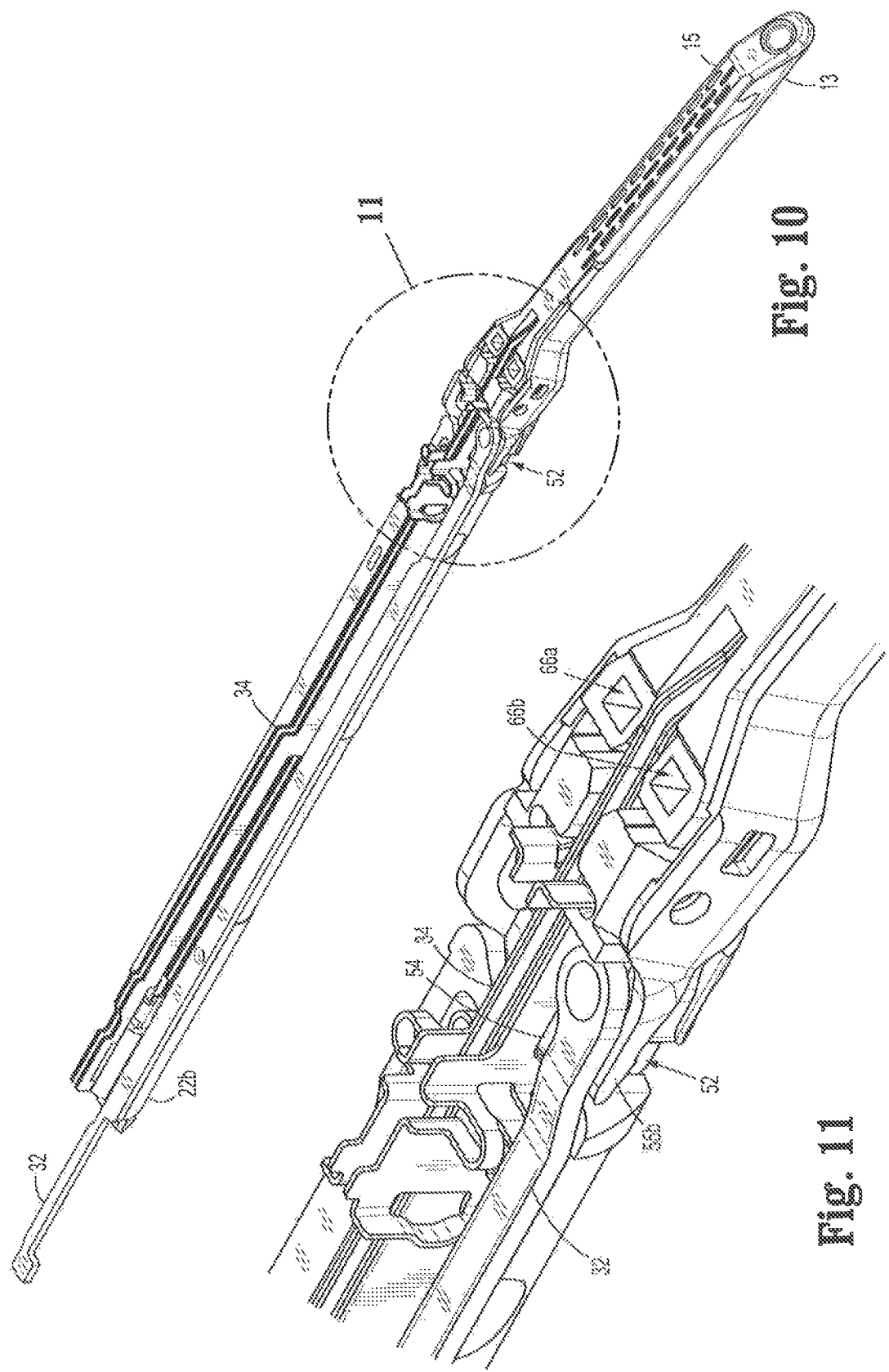

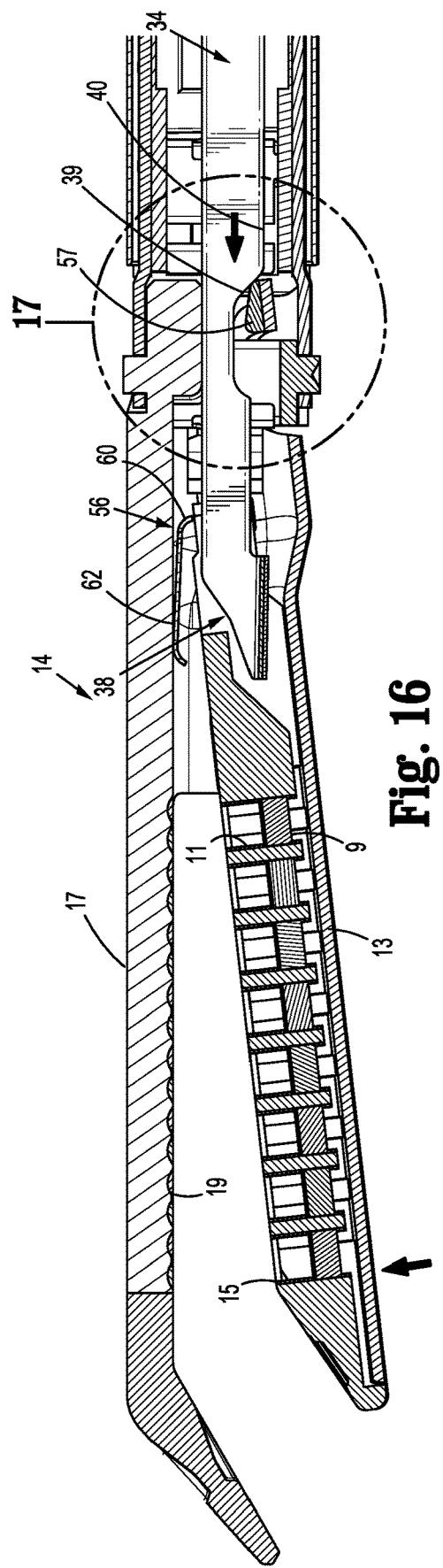
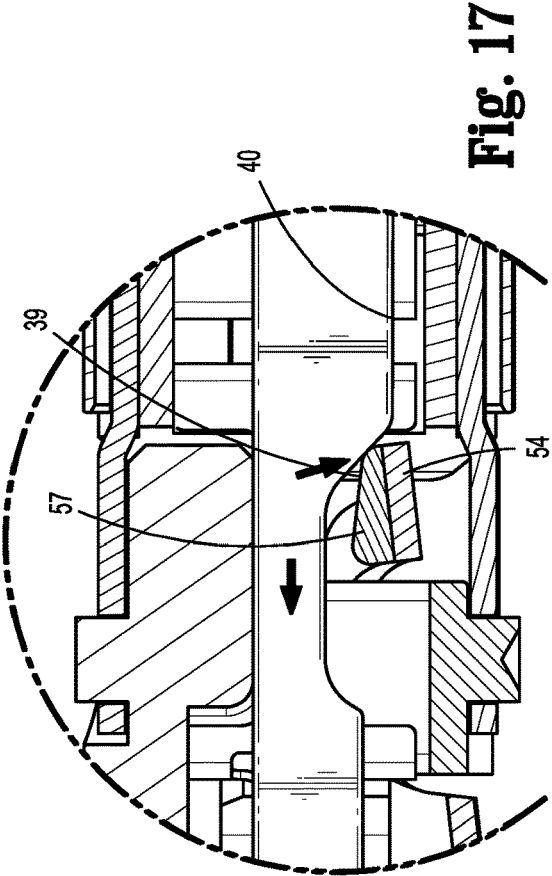

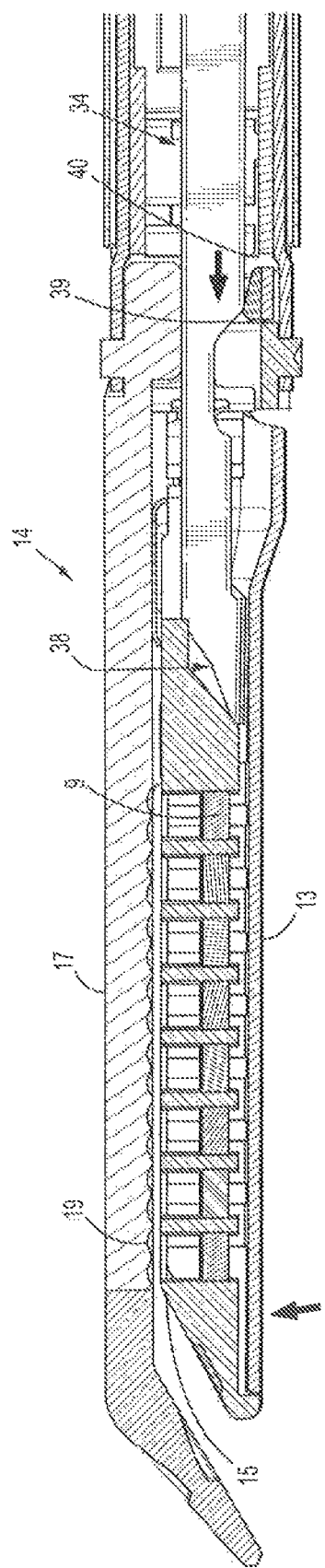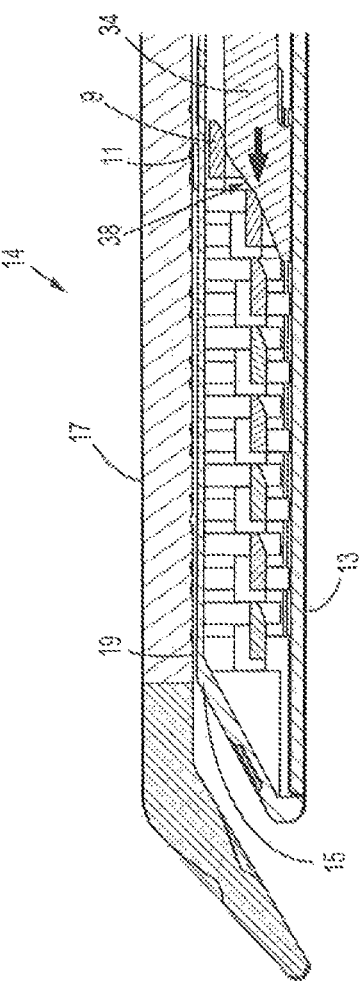
Fig. 18
Fig. 19

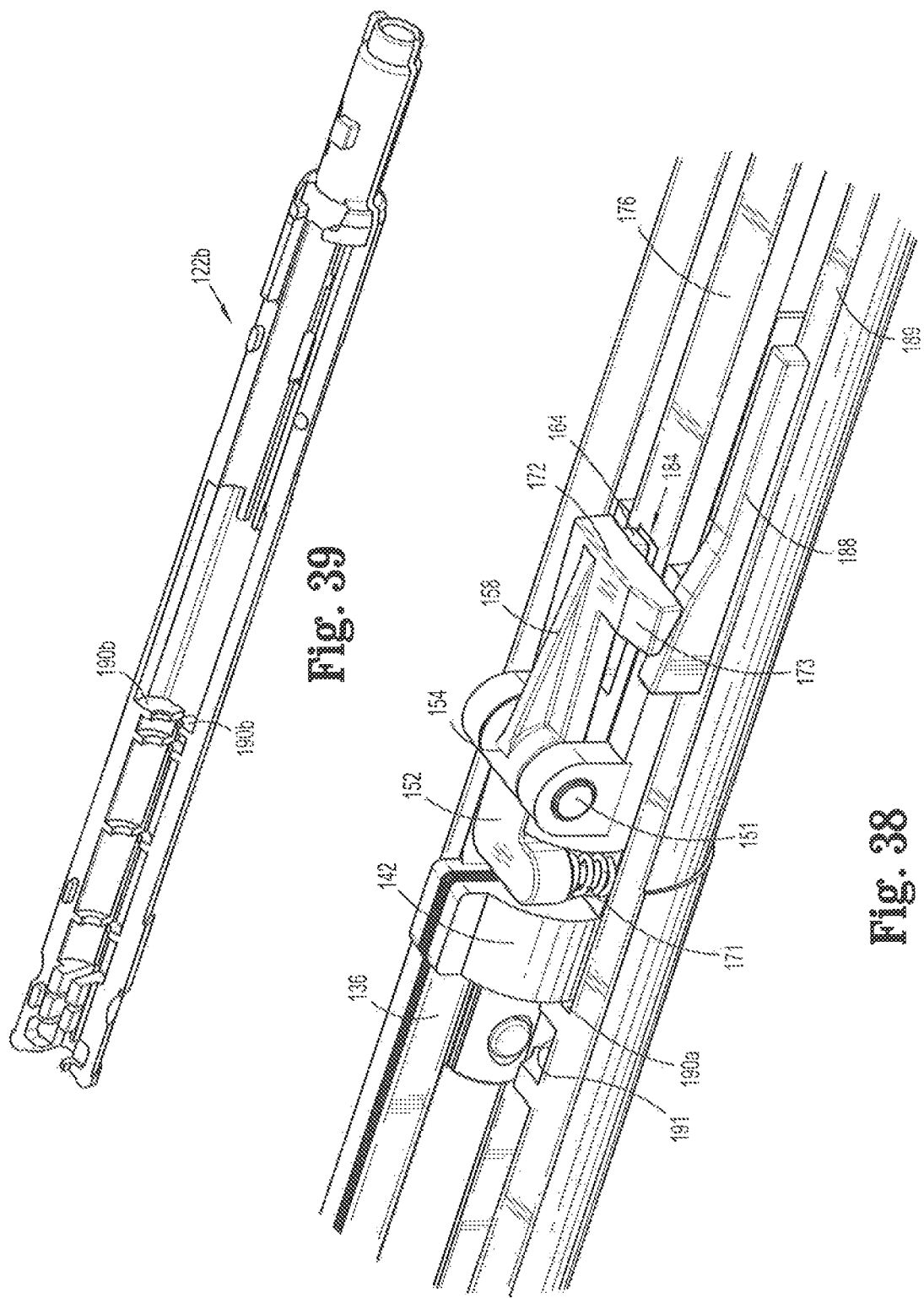

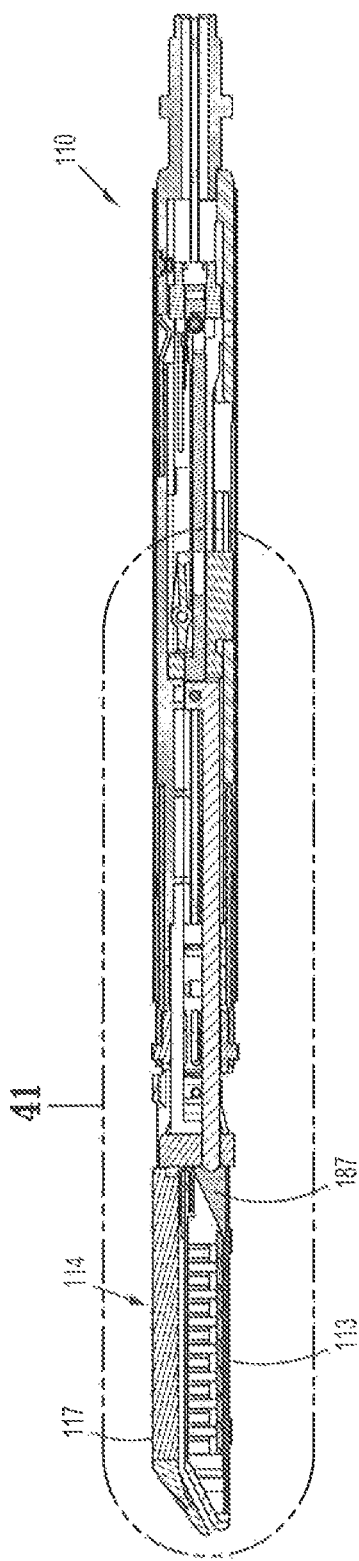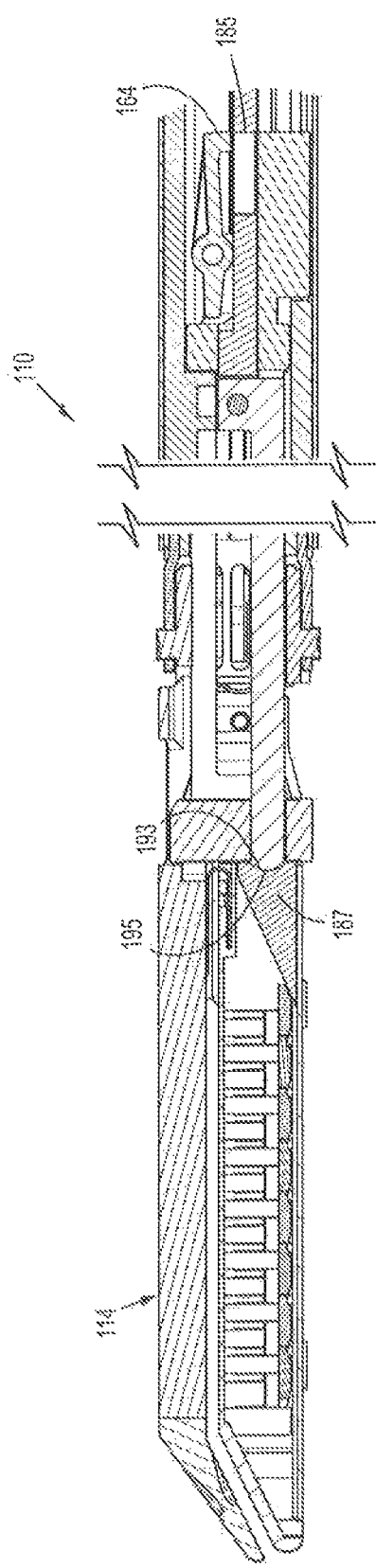
Fig. 40
Fig. 41

SURGICAL APPARATUS

CROSS-REFERENCE TO RELATED APPLICATIONS

This application is a continuation which claims the benefit of and priority to U.S. patent application Ser. No. 14/166,366, filed Jan. 28, 2014, the entire disclosure of which is incorporated by reference herein.

BACKGROUND

Technical Field

The present disclosure relates to a surgical apparatus. More specifically, the present disclosure relates to a surgical stapler including firing assemblies configured to control tissue gap distance between jaw members of the stapler when the jaw members are in a clamping configuration and the surgical stapler is fired.

Description of Related Art

Surgical staplers configured to clamp and staple tissue are known. Such staplers may include a tool assembly that is supported at a distal end of a shaft of the stapler. The tool assembly may, for example, include an anvil and a cartridge including a plurality of fasteners that are configured to staple tissue (e.g., occlusion of vascular structure during a transplant procedure).

To staple tissue with such staplers, tissue can be positioned between the cartridge and anvil, and the anvil can be approximated towards the cartridge to clamp the tissue. Once tissue is clamped, the stapler can be fired to advance the drive assembly of the stapler distally through the cartridge to eject the plurality of surgical fasteners sequentially from the cartridge to staple tissue.

In addition to the mechanisms recited to fire the plurality of fasteners, conventional staplers may further include a structure configured to control tissue gap distance between the anvil and the cartridge of the tool assembly during firing of the stapler.

While the aforementioned staplers may be satisfactory for the above uses, there may exist a need for a simpler design for firing surgical fasteners and/or approximating a cartridge towards an anvil. There is also a need for a firing assembly that takes up less space, as well as a need for an alternative approximation assembly and/or method.

SUMMARY

An aspect of the present disclosure provides a surgical stapling apparatus. The surgical stapling apparatus includes an actuating device including an elongated shaft. A tool assembly is disposed on a distal end of the shaft. The tool assembly may be removably couplable to the distal end of the shaft of the surgical stapling apparatus. The tool assembly includes a first jaw member supporting a cartridge assembly having a plurality of surgical fasteners, and a second jaw member supporting an anvil. The first jaw member is movable in relation to the second jaw member between a spaced position and an approximated position. One of the first and second jaw members includes a cantilever at a proximal end thereof. The cantilever may be in the form of a bridge that extends transverse in relation to a longitudinal axis defined through the shaft of the surgical stapling apparatus. A firing cam bar assembly is slidably disposed within the tool assembly. The firing cam bar assembly includes a cam surface configured to engage the cantilever to move the first and second jaw member towards the approximated position and a distal end configured to deploy the plurality of surgical fasteners from the cartridge as the firing cam bar assembly is translated distally through the tool assembly.

The firing cam bar assembly may include a first firing cam bar having an elongated configuration and a distal portion defining the cam surface. The surgical stapler may further include a second firing cam bar having an elongated configuration and a distal portion defining the cam surface, the second firing cam bar seated within the first firing cam bar. The cartridge may include a plurality of pushers and the distal portions of the first and second firing cam bars are configured to contact the plurality of pushers of the cartridge to deploy the plurality of surgical fasteners from the cartridge.

The cam surface of the firing cam bar assembly may include a first cam portion disposed distally and at an angle in relation to a second cam portion. The second cam portion of the cam surface may taper inwardly toward a proximal end of the firing cam bar assembly.

A resilient member may be provided on the cartridge for biasing the cartridge radially away from the anvil. The resilient member may include a proximal end that is coupled to a proximal end of the cartridge and a distal end that is positioned to contact at least a portion of the anvil. The proximal end of the resilient member may include two finger portions that are seated within two corresponding apertures defined at the proximal end of the cartridge.

An aspect of the present disclosure provides a reload configured for use with a surgical stapling apparatus. The reload includes a shaft including a proximal end, which is adapted to couple to a surgical apparatus, and distal end. A tool assembly is disposed on the distal end of the shaft. The tool assembly includes a first jaw member supporting a cartridge assembly having a plurality of surgical fasteners, and a second jaw member supporting an anvil. The first jaw member is movable in relation to the second jaw member between a spaced position and an approximated position. One of the first and second jaw members includes a cantilever at a proximal end thereof. The cantilever may be in the form of a bridge that extends transverse in relation to a longitudinal axis defined through the shaft of the surgical stapling apparatus. A firing cam bar assembly is slidably disposed within the tool assembly. The firing cam bar assembly includes a cam surface configured to engage the cantilever to move the first and second jaw member towards the approximated position and a distal end configured to deploy the plurality of surgical fasteners from the cartridge as the firing cam bar assembly is translated distally through the tool assembly.

An aspect of the present disclosure provides a surgical stapling apparatus. The surgical stapling apparatus includes an actuating device including an elongated shaft. A tool assembly is disposed on a distal end of the shaft. The tool assembly is removably couplable to the distal end of the shaft of the surgical stapling apparatus. The tool assembly includes a first jaw member supporting a cartridge assembly having a plurality of fasteners and a sled positioned to eject the fasteners from the cartridge assembly and a second jaw member supporting an anvil. The first jaw member is movable in relation to the second jaw member between spaced and approximated positions. A sled pusher assembly includes a sled pusher having a distal end configured to engage the sled of the cartridge assembly. A drive beam assembly includes a latch assembly having a latch releasably coupled to the sled pusher assembly. Distal translation of the drive beam assembly from a retracted position towards an advanced position effects movement of the first and second jaw members to the approximated position and disengages the latch of the latch assembly from the sled pusher assembly to facilitate distal movement of the sled pusher independently of the drive beam assembly. Distal movement of the sled pusher independently of the drive beam assembly also advances the distal end of the sled pusher into engagement with the sled of the cartridge assembly to eject the plurality of fasteners from the cartridge assembly.

The latch assembly may include a collar which is coupled to a proximal end of the drive beam assembly and may include an aperture configured to receive a support member of the sled pusher assembly. The support member of the sled pusher assembly may include at least one aperture that is configured to receive the latch of the latch assembly.

The drive beam assembly may include an I-beam having a sidewall defining a notch, the sled pusher being received within the notch. The I-beam may be positioned to cam the first and second jaw members to the approximated position when the drive beam assembly is translated distally.

The latch assembly may include at least one spring configured to bias the latch of the latch assembly into the aperture defined in the support member of the sled pusher assembly. The aperture of the support member may be defined by a proximal wall portion of the sled pusher assembly. The proximal wall portion may be configured to engage the latch of the latch assembly to maintain the drive beam assembly and the sled pusher coupled with one another.

The elongated shaft may include upper and lower housing portions, and at least one of the upper and lower housing portions includes at least one stop member configured to contact a proximal end of the collar of the latch assembly when the drive beam assembly is translated distally. The latch may include a lateral offset extension, and wherein at least one of the upper and lower housing portions of the elongated shaft includes at least one ramp portion configured to be engaged by the lateral offset extension to effect movement of the latch out of engagement with the proximal wall portion when the drive beam assembly is moved distally so as to allow the sled pusher assembly to move distally in relation to the drive beam assembly.

A resilient member may be provided on the cartridge for biasing the cartridge assembly radially away from the anvil. The resilient member may include a bottom portion that is coupled to a proximal end of the cartridge and a top portion that is positioned to contact at least a portion of the anvil. The bottom portion of the resilient member may be seated within a corresponding slot defined at the proximal end of the cartridge assembly. The bottom portion of the resilient member may include at least one detent that couples to a corresponding indent disposed on the cartridge assembly adjacent the slot.

An aspect of the present disclosure provides a reload configured for use with a surgical stapling apparatus. The reload includes a shaft including a proximal end and distal end. The proximal end adapted to couple to a surgical apparatus. A tool assembly is disposed on the distal end of the shaft. The tool assembly includes a first jaw member supporting a cartridge assembly having a plurality of fasteners and a sled positioned to eject the fasteners from the cartridge assembly and a second jaw member supporting an anvil. The first jaw member is movable in relation to the second jaw member between spaced and approximated positions. A sled pusher assembly includes a sled pusher having a distal end configured to engage the sled of the cartridge assembly. A drive beam assembly includes a latch assembly having a latch releasably coupled to the sled pusher assembly. Distal translation of the drive beam assembly from a retracted position towards an advanced position effects movement of the first and second jaw members to the approximated position and disengages the latch of the latch assembly from the sled pusher assembly to facilitate distal movement of the sled pusher independently of the drive beam assembly. Distal movement of the sled pusher independently of the drive beam assembly also advances the distal end of the sled pusher into engagement with the sled of the cartridge assembly to eject the plurality of fasteners from the cartridge assembly.

BRIEF DESCRIPTION OF THE DRAWING

Various embodiments of the present disclosure are described hereinbelow with references to the drawings, wherein:

FIG. 2 is an exploded view of the reload shown in FIG. 1A with parts separated;

FIG. 3 is a perspective view of a firing cam bar assembly of the reload shown in FIGS. 1 and 2;

FIG. 4 is the indicated area of detail shown in FIG. 3;

FIG. 5 is a side view of the firing cam bar assembly shown in FIG. 3;

FIG. 6 is an exploded view of the firing cam bar assembly shown in FIG. 3 with parts separated;

FIG. 8 is a perspective view of the reload shown in FIG. 1A with an outer tube of the reload removed;

FIG. 9 is the indicated area of detail shown in FIG. 8;

FIG. 10 is a perspective view of the reload shown in FIG. 1A with parts removed illustrating the firing cam bar assembly coupled to a cartridge of a tool assembly of the reload;

FIG. 11 is the indicated area of detail shown in FIG. 10;

FIG. 16 is a partial, cross sectional view of a distal end of the reload shown in FIG. 1A illustrating the firing cam bar assembly being translated through the cartridge to fire fasteners of the cartridge;

FIG. 17 is the indicated area of detail shown in FIG. 16;

FIG. 18 is a partial, cross sectional view of the distal end of the reload shown in FIG. 15 illustrating a cam surface of the firing cam bar assembly sliding along the cantilever of the cartridge as the firing cam bar assembly is being translated through the cartridge to fire fasteners of the cartridge;

FIG. 19 is a partial, cross sectional view of the distal end of the reload shown in FIG. 15 illustrating a pusher contacting surface of the firing cam bar assembly pushing a pusher of the cartridge as the firing cam bar assembly is being translated through the cartridge to fire fasteners of the cartridge;

FIG. 38 is the indicated area of detail shown in FIG. 37;

FIG. 39 is a perspective view of an upper shaft portion of the reload shown in FIG. 21;

FIG. 40 is a cross sectional view of the reload shown in FIG. 21 with the distal end of the reload shown in the clamped configuration;

FIG. 41 is the indicated area of detail shown in FIG. 40;

DETAILED DESCRIPTION

Figure 1A:
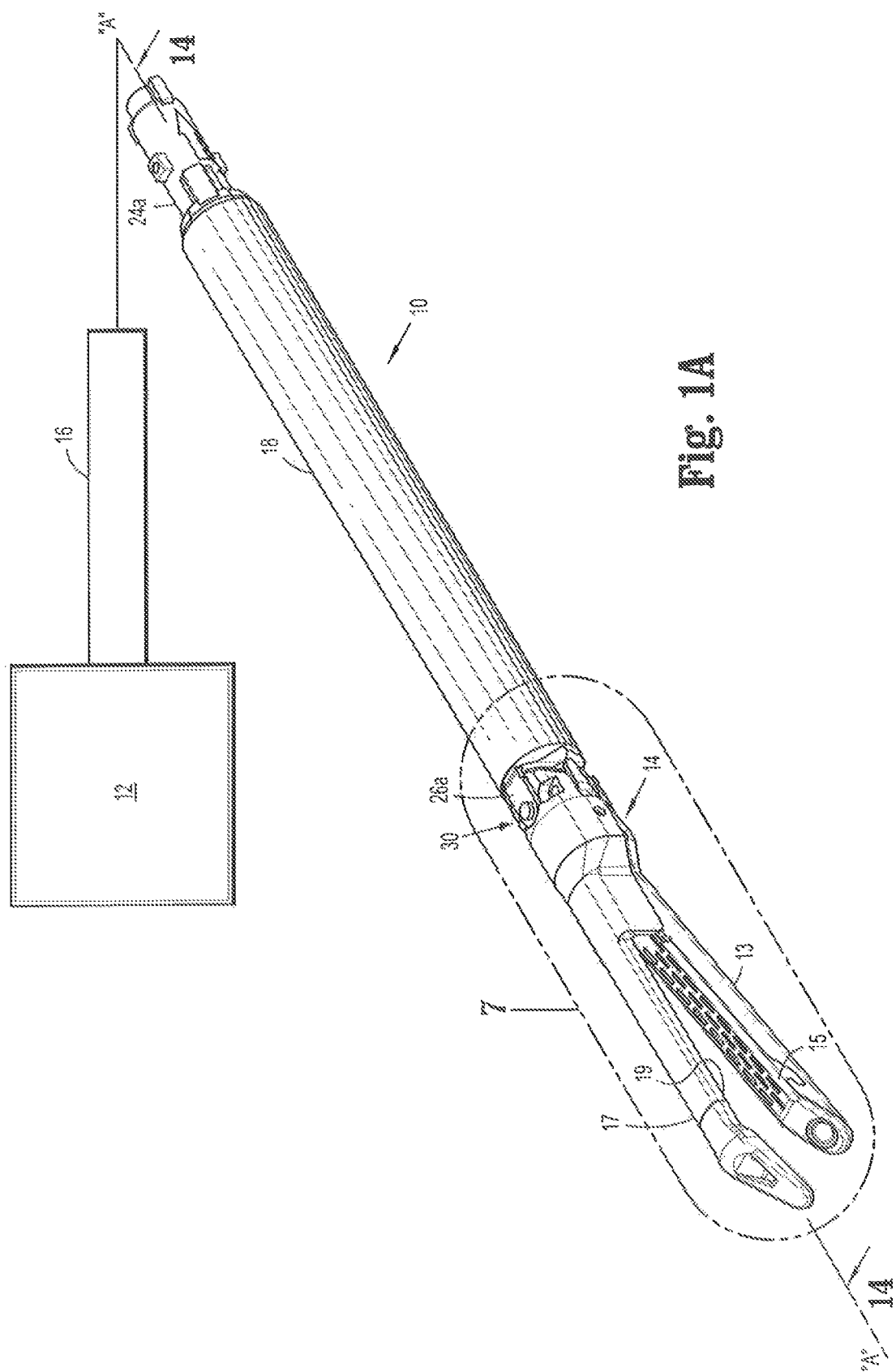
FIG. 1A is a perspective view of a reload according to an embodiment of the instant disclosure, the reload configured for use with a surgical apparatus that is shown schematically in FIG. 1A.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Referring initially to FIG. 1A, a reload 10 in accordance with the present disclosure is shown. The reload 10 may be configured to be coupled to a variety of different surgical actuating devices, shown schematically as 12 in FIG. 1A, including manually operated actuation devices, robotically controlled actuation devices, electromechanical actuation devices, motorized actuation devices, etc. The surgical actuating device 12 includes a shaft assembly 16 having a distal end configured to releasably support the reload 10.

Figure 1B:
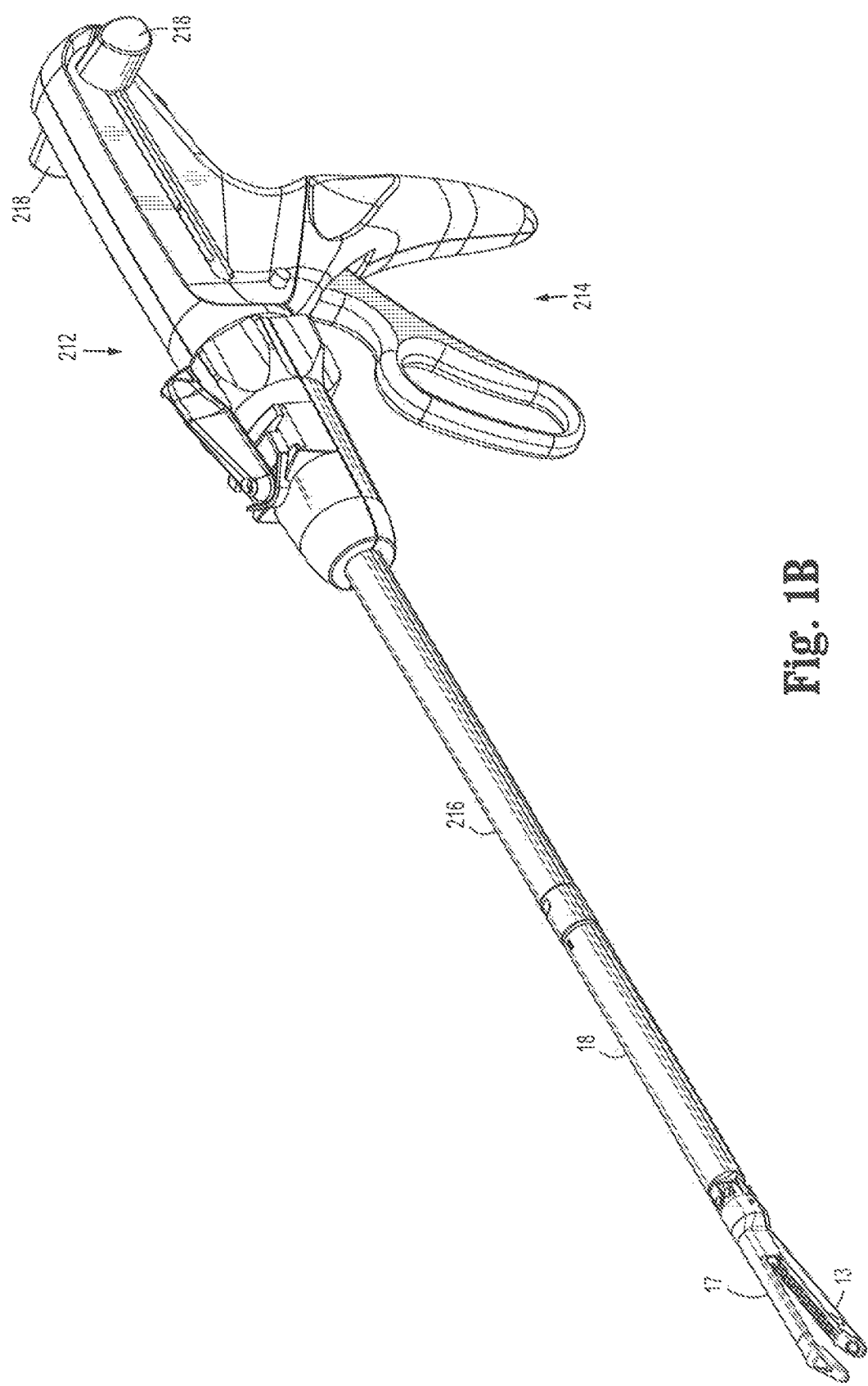
FIG. 1B is a perspective view of one type of surgical stapler that may be utilized with the reload shown in FIG. 1A.
Figure 7:
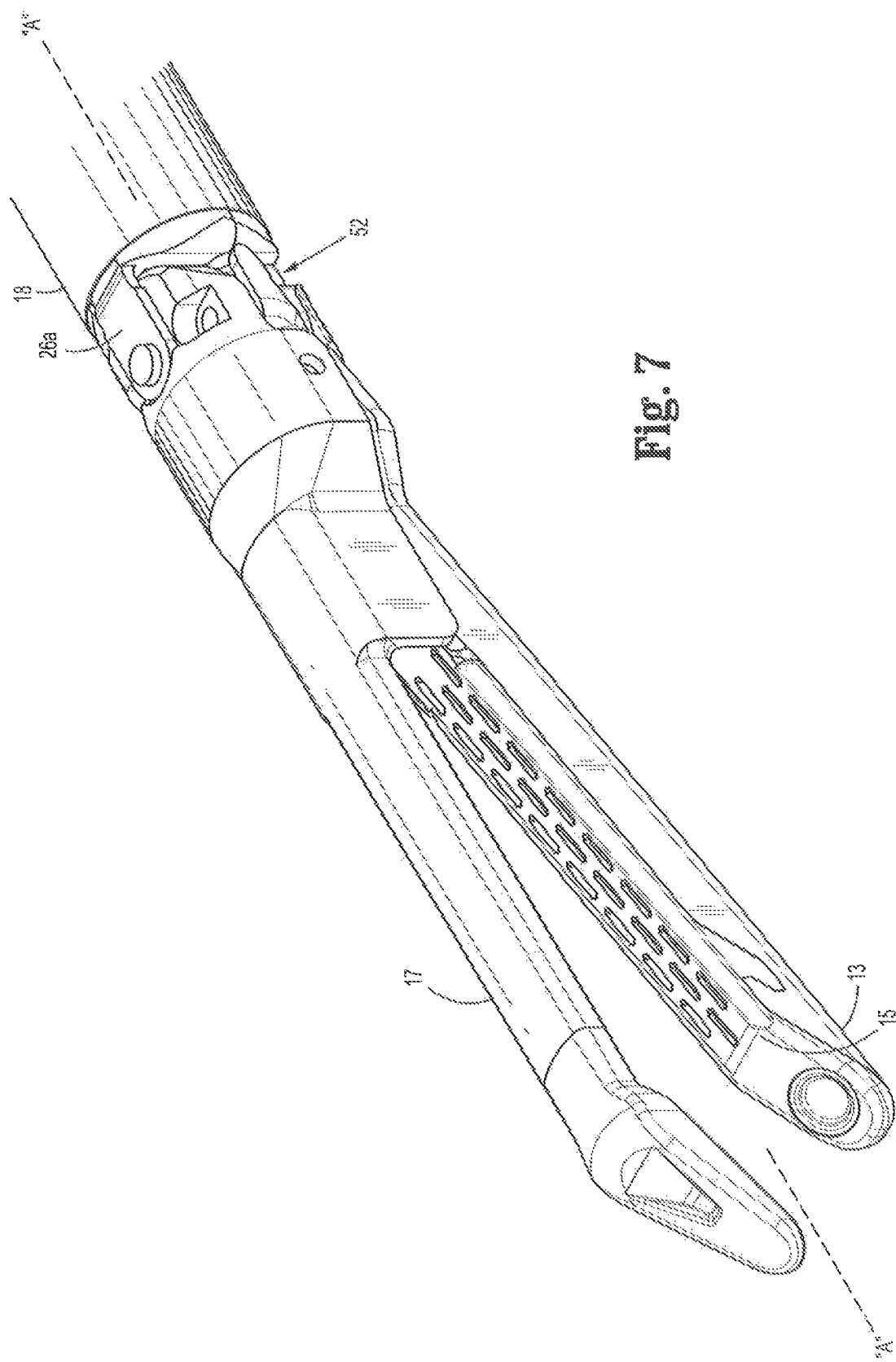
FIG. 7 is the indicated area of detail shown in FIG. 1A.
Figure 12:
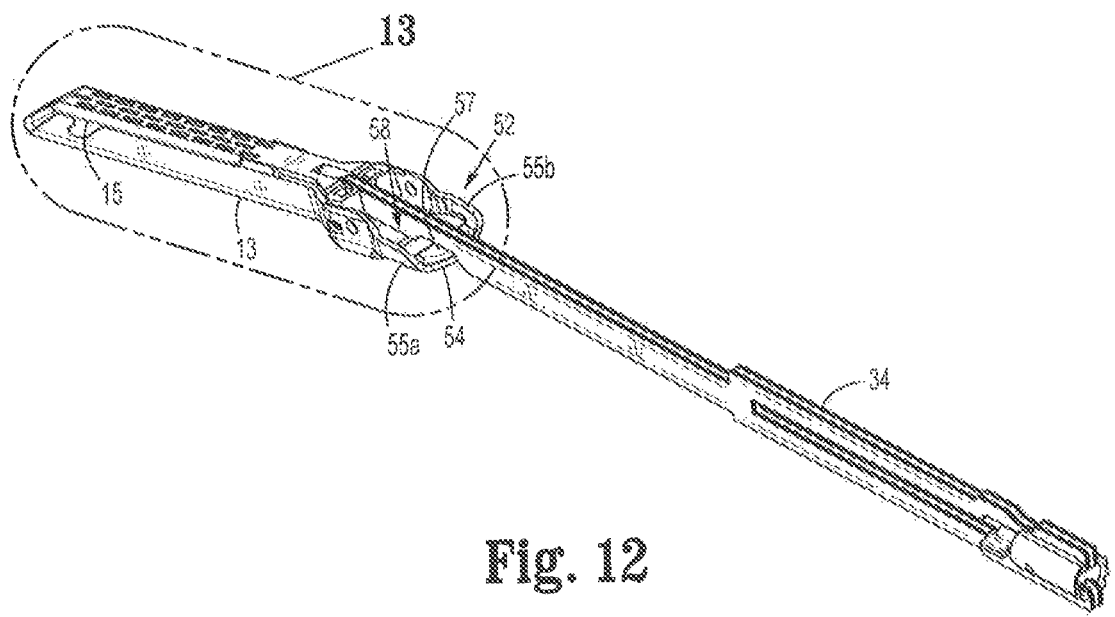
FIG. 12 is a perspective view of the reload shown in FIG. 1A with parts removed illustrating a cantilever of the cartridge in contact with the firing cam bar assembly.

In one embodiment illustrated in FIG. 1B, the surgical actuating device 12 is a manually operated stapler 212 which includes a handle assembly 214 and a shaft assembly 216 that engages and supports the reload 10. The handle assembly 214 includes a pair of retraction knobs 218 that is configured to return the stapler 212 to a retracted configuration. For a more detailed description of the operation and the operative components of the stapler 212, reference is made to commonly-owned U.S. Pat. No. 5,865,361 to Milliman, the entire contents of which are hereby incorporated by reference.

FIG. 2 is a perspective view of the reload 10 with parts separated. The reload 10 includes an outer tube 18 that houses a shaft assembly 20 configured to couple the reload 10 to the shaft assembly 16 of the actuating device 12 (see FIG. 1A). The shaft assembly 20 includes an upper housing portion 22a and lower housing portion 22b that, when coupled to one another, house components of the reload 10. Proximal ends 24a, 24b of the upper and lower housing portions 22a, 22b are configured to releasably couple with the distal end of the shaft assembly 16 of the actuating device 12 (e.g., see the '361 patent). A distal end of the housing portions 22a, 22b of the shaft assembly 20 supports upper and lower coupling members 26a, 26b respectively. A distal end of each of coupling members 26a, 26b is configured to pivotally engage upper and lower pivot portions 28a, 28b, respectively, of a pivot assembly 30 (see FIG. 1A). An articulating link 32 is slidably positioned within the upper and lower housing portions 22a, 22b and is configured to articulate an end effector or tool assembly 14 of the reload 10 in relation to the shaft assembly 20.

The tool assembly 14 includes a first jaw member 13 that supports a cartridge 15 and a second jaw member 17 that supports an anvil 19. The first jaw member 13 is pivotally supported in relation to the second jaw member 17 between spaced and approximated positions. The cartridge 15 houses a plurality of pushers 9 and fasteners 11. A dissecting tip 19a may be secured to a distal end of the anvil 19 to facilitate positioning of the anvil 19 in relation to tissue to be stapled. Such a dissecting tip 19a is described in U.S. Pat. No. 8,348,123 which is hereby incorporated herein by reference.

Referring also to FIGS. 3-6, the shaft assembly 20 includes a firing cam bar assembly 34 that is releasably engaged with a central rod (not shown) of the actuating device 12. The firing cam bar assembly 34 is configured to move the cartridge 15 from the spaced position (FIG. 1B) towards the anvil 19 to the approximated position (FIG. 18) as the firing cam bar assembly 34 is translated distally through the tool assembly 14. A distal end of the firing cam bar assembly 34 is also configured to push the plurality of pushers 9 to fire the plurality of fasteners 11 from the cartridge 15 as the firing cam bar assembly 34 is translated through the cartridge 15 as will be described in further detail below.

The firing cam bar assembly 34 includes a first firing cam bar 36 having an elongated configuration defined by left and right sidewalls 37a, 37b, which have a distal end 38. Each of the left and right sidewalls 37a and 37b of the cam bar 36 includes a cam surface 33 having a first cam portion 39 and a second cam portion 40. Each of the first cam portions 39 is disposed distally and at an angle in relation to one of the second cam portions 40 which is defined along a bottom/lower surface of the left and right sidewalls 37a, 37b. Only one of the second cam portions 40 can be seen in FIGS. 3-5. The configuration of the first cam portions 39 of the cam surface 33 facilitates movement of the first jaw member 13 towards the second jaw member 17 from the spaced position to the approximated position so that tissue may be clamped as will be described in further detail below. The second cam portions 40 are elongated in comparison to the first cam portions 39 and taper inwardly a distance "T" (FIG. 5) in relation to a longitudinal axis "B-B" of the firing cam bar assembly 34 toward a proximal end of the firing cam bar assembly 34 (FIG. 5). The taper "T" controls a tissue gap distance between the first and second jaw members 13, 17 when the first and second jaw members 13, 17 are moved toward the approximated position, as will be described in further detail below.

The distal end 38 of the first firing cam bar 36 includes two pusher contacting surfaces 42a, 42b (FIGS. 4 and 6) which are aligned with the plurality of pushers 9 of the cartridge 15 (FIG. 19). The pusher contacting surfaces 42a, 42b are configured to contact the plurality of pushers 9 to deploy the plurality of surgical fasteners 11 from the cartridge 15.

In the illustrated embodiment, the firing cam bar assembly 34 includes a second or inner firing cam bar 44 that is similar to the first firing cam bar 36. The first and second firing cam bars 36, 44 form a nested configuration with one another (as best shown in FIG. 6). The second firing cam bar 44 has an elongated configuration defined by left and right sidewalls 45a, 45b, which have a distal end 46. Each of the left and right sidewalls 45a and 45b of the cam bar 44 includes a cam surface 53 having a first cam portion 49 and second cam portion 50. The first cam portions 49 of the cam surface 53 are disposed distally and at an angle in relation to the second cam portions 50 (only one of the second portions 50 is shown) of the cam surface 53. The distal end 46 of the second firing cam bar 44 includes two pusher contacting surfaces 48a, 48b which are aligned with the plurality of pushers 9 of the cartridge 15 to contact the plurality of pushers 9 to deploy the plurality of surgical fasteners 11 from the cartridge 15 (FIG. 19).

The first and second firing cam bars 36, 44 may be formed from any suitable material including, but not limited to, plastic, metal, etc. In embodiments, the first and second firing cam bars 36, 44 are formed from metal.

While the firing cam bar assembly 34 has been described herein as including first and second firing cam bars 36, 44, greater or fewer firing cam bars may be utilized. For example, in embodiments, the second firing cam bar 44 may be omitted. In this particular embodiment, the configuration of the first firing cam bar 36 of the firing cam bar assembly 34 may be modified to include features of the second firing cam bar 44. For example, the left and right sidewalls 37a, 37b of the first firing cam bar 36 may be widened at the distal end 38 to align with all of the rows of the plurality of pushers 9 for ejecting all of the plurality of fasteners 11 disposed within the cartridge 15. Alternately, the second firing cam bar 44 can be omitted with no change to the configuration of the first firing cam bar 36.

Referring to FIGS. 7-13, a cantilever 52 (FIG. 13) is provided at a proximal end of the first jaw member 13. The cantilever 52 may be monolithically formed with the first jaw member 13. Alternatively, the cantilever 52 may be formed as a separate component apart from the first jaw member 13 and coupled to the first jaw member 13 via one or more suitable coupling methods, e.g., welding. The cantilever 52 is disposed adjacent the pivot assembly 30 between the lower coupling member 26b and a distal end of the articulating link 32 (see FIG. 9 for example).

Figure 13:
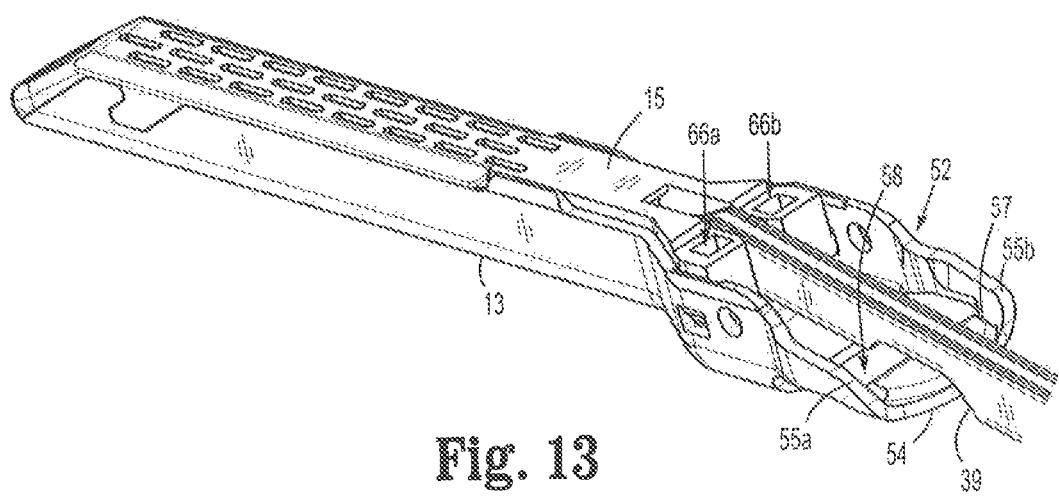
FIG. 13 is the indicated area of detail shown in FIG. 12.

In the illustrated embodiment, the cantilever 52 is in the form of a bridge 54 that is formed between side projections 55a, 55b that extend proximally from the proximal end of the first jaw member 13 (FIG. 13). The bridge 54 is disposed transverse to a longitudinal axis "A-A" (FIG. 7) defined through the shaft assembly 20 of the reload 10.

The bridge 54 supports a cam member 57 (FIGS. 2 and 13) which is positioned to be slidably engaged by the first and second cam portions 39, 49 and 40, 50, respectively, of the first and second firing cam bars 36, 44 when the firing cam bar assembly 34 is advanced distally within the cartridge 15, as will be described in greater detail below. The cam member 57 may be slanted (as shown in the illustrated embodiment) or otherwise configured to operate in conjunction with the taper "T" of the second cam portions 40, 50 of the first and second cam bars 36, 44, respectively, to control the size of the tissue gap between the first and second jaw members 13, 17 when the first and second jaw members 13, 17 are in the approximated configuration. The cam member 57 may be coupled to the bridge 54 via one or more suitable coupling methods, e.g., adhesive, welding, etc. Alternatively, the cam member 57 may be omitted and the bridge 54 may be integrally formed with a cam surface configured to control the size of the tissue gap. In accordance with the instant disclosure, the bridge 54 engages the firing cam bars 36, 44 to close the first and second jaw members 13, 17 in both the linear and articulated positions.

Referring to FIG. 9, the cantilever 52 defines an aperture 58 between the side projections 55a, 55b and the bridge 54. The aperture 58 receives a rivet 59 (FIG. 9) for coupling the lower coupling member 26b to the lower portion 28b of the pivot assembly 30 during manufacture of the reload 10.

Figure 14:
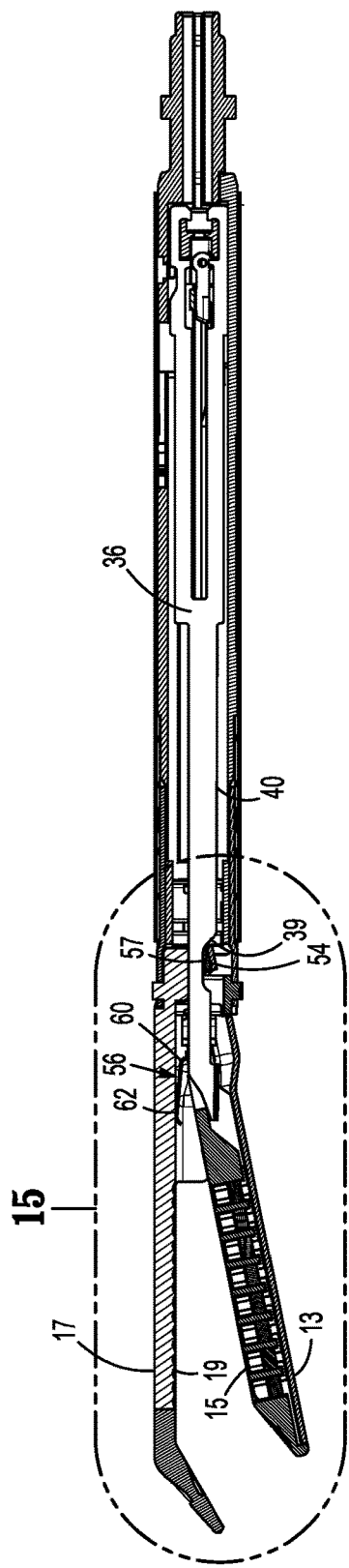
FIG. 14 is a cross sectional view taken along section line 14-14 in FIG. 1A.
Figure 15:
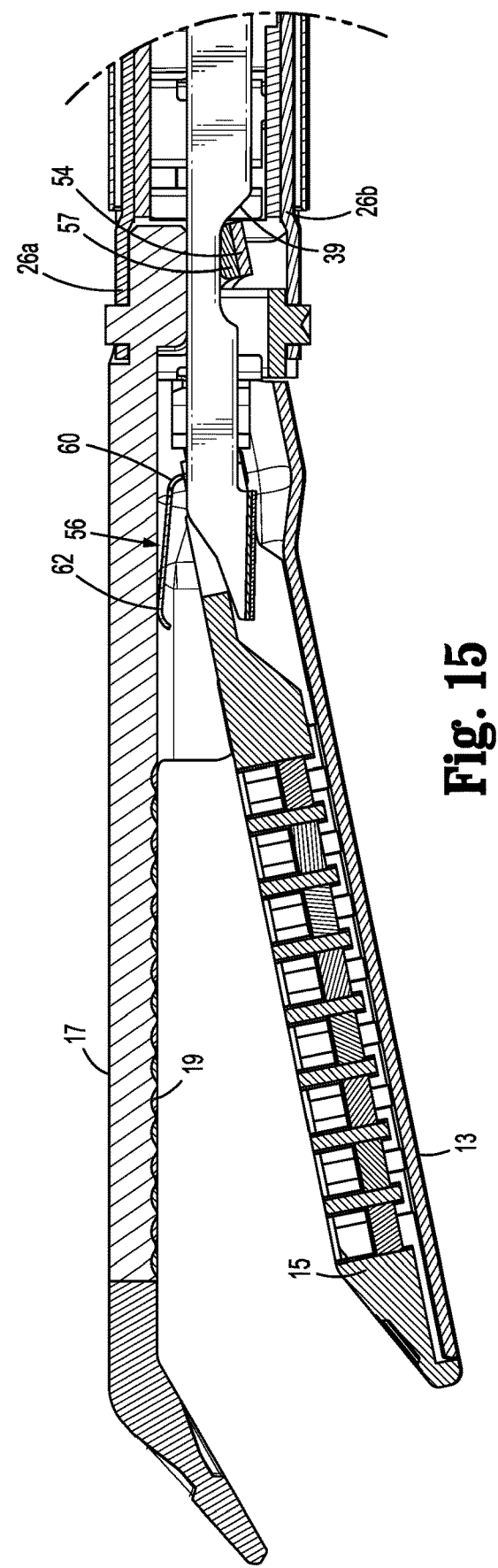
FIG. 15 is the indicated area of detail shown in FIG. 14.

Referring to FIGS. 2, 14, and 15, a resilient member 56 is provided on the cartridge 15 and is positioned to bias the cartridge 15 radially away from the anvil 19 towards the spaced position. The resilient member 56 includes a proximal end 60 that is coupled to a proximal end of the cartridge 15 and a distal end 62 that is positioned to contact at least a portion of the anvil 19. In the illustrated embodiment, the proximal end 60 of the resilient member 56 includes two finger portions 64a, 64b that seat within two corresponding apertures 66a, 66b of suitable configuration defined at the proximal end of the cartridge 15 (see FIG. 2 and FIG. 13).

Referring to FIGS. 16 and 17, in use, prior to positioning tissue between the first and second jaw members 13, 17, the tool assembly 14 is in the spaced or unapproximated position. In this position, the distal ends 38, 46 of the first and second firing cam bars 36, 44 are positioned proximally of the plurality of pushers 9 and the plurality of fasteners 11. In addition, in this configuration an engagement portion of the first cam portions 39, 49 (see also FIG. 6) of the first and second firing cam bars 36, 44 is positioned proximally of the cam member 57. As discussed above, the resilient member 56 is positioned to urge the jaw member 13 to the spaced or unapproximated position.

Referring to FIG. 18, when the firing cam bar assembly 34 is advanced distally, the first cam portions 39, 49 of the first and second firing cam bars 36, 44 and engage the cam member 57 of the bridge 54 and pivot the first jaw member 13 including the cartridge 15 towards the anvil 19 of the second jaw member 17 to move the jaw member 13 including the cartridge 15 to the clamped or approximated configuration. In this example, the cartridge is pivotably attached to the second jaw member. However, any of the embodiments disclosed herein can have a first jaw member, or second jaw member, or both that are pivotably movable.

Figure 20:
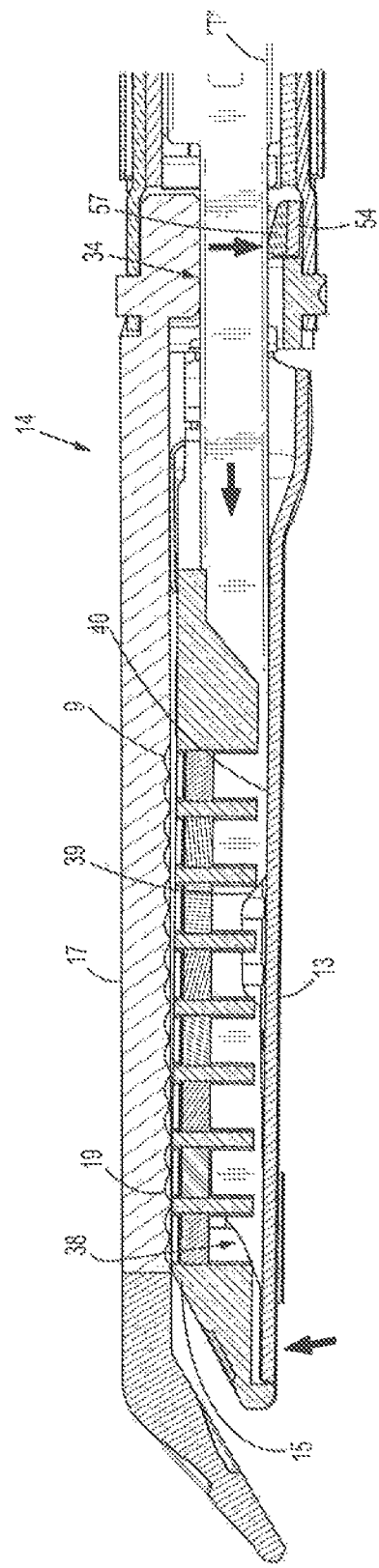
FIG. 20 is a partial, cross sectional view of the distal end of the reload shown in FIG. 15 illustrating the cam surface of the firing cam bar assembly and the cantilever of the cartridge in contact with one another to maintain a specific tissue gap distance between the cartridge and an anvil of the tool assembly.
Figure 21:
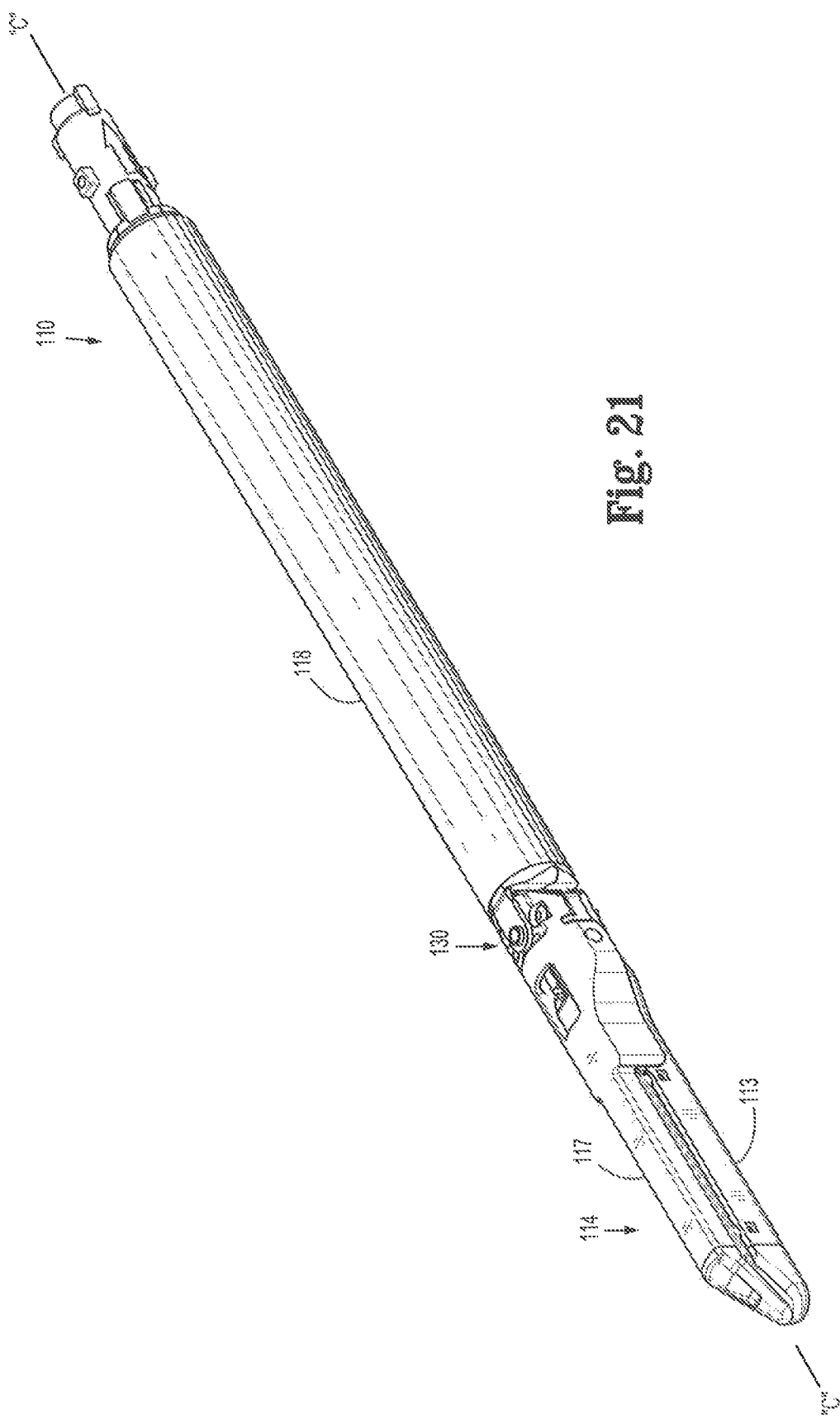
FIG. 21 is a perspective view of a reload according to another embodiment of the instant disclosure, the reload configured for use with the surgical apparatus that is shown schematically in FIG. 1A.

Referring to FIG. 19, continued distal translation of the firing cam bar assembly 34 moves the distal ends 36, 48 of the first and second firing cam bars 36, 44 into contact with the plurality of pushers 9 sequentially to eject the plurality of fasteners 11 from the cartridge 15 and into the anvil 19 to staple clamped tissue. In accordance with the present disclosure, as the firing cam bar assembly 34 is translated through the cartridge 15, engagement of the cam member 57 on the bridge 54 with the taper "T" (FIG. 15) on the second cam portions 40, 50 of the first and second firing cam bars 36, 44 controls the position of the jaw member 17 in relation to the jaw member 13 to selectively maintain a desired tissue gap distance between the first and second jaw members 13, 17 (FIG. 20). In accordance with the instant disclosure, the degree of the taper "T" on the second cam portions 40, 50 of the first and second firing cam bars 36, 44 may be uniform or non-uniform to selectively control the tissue gap distance during translation of the cam bar assembly 34 through the cartridge 15. It is noted that the taper "T" may define a positive or negative slope in the proximal direction to provide the proper or desired tissue gap distance.

The unique configuration of the jaw member 13 including the firing cam bar assembly 34 and cantilever 52 provides a simple design for approximating and controlling the tissue gap between the cartridge 15 and the anvil 19. Additionally, the presently disclosed tool assembly 14 allows for the tissue gap between the first and second jaw members 13, 17 to be accurately controlled by the second cam portions 40, 50 of the first and second firing cam bars 36, 44 as the firing cam bar assembly 34 is advanced.

In embodiments, the tool assembly 14 can be integrally formed with the surgical actuating device 12. In this particular embodiment, the tool assembly 14 can be operably coupled to an articulating assembly, e.g., the articulating assembly 30, which may be supported at a distal end of the shaft assembly 16 of the surgical actuating device 12. Alternatively, the articulating assembly 30 can be omitted and the tool assembly 14 can be directly connected to the distal end of the shaft assembly 16 of the surgical actuating device 12.

FIGS. 21-44 illustrate a reload 110 according to another embodiment of the instant disclosure. The reload 110 is configured for use with the stapler 212 that is shown in FIG. 1B. Only the features that are unique to the reload 110 are described herein.

Figure 22:
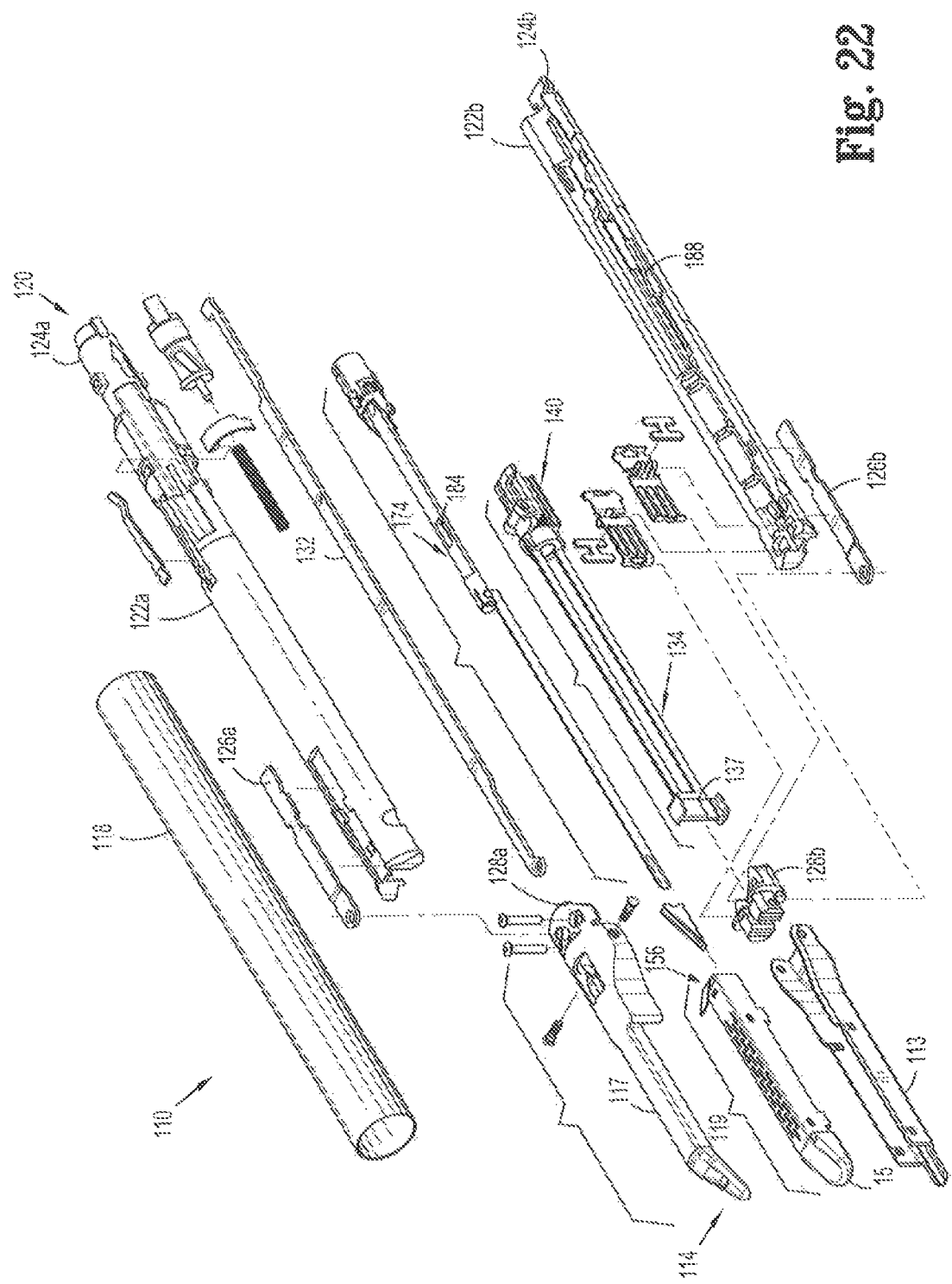
FIG. 22 is an exploded view of the reload shown in FIG. 21 with parts separated.

FIG. 22 is a perspective view of the reload 110 with parts separated. The reload includes an outer tube 118 that houses a shaft assembly 120 configured to couple the reload 110 with the shaft assembly 216 of the actuating device 212 shown in FIG. 1B. The shaft assembly 120 includes upper housing portion 122a and lower housing portion 122b that, when coupled to one another, house components of the reload 110. Proximal ends 124a, 124b of the upper and lower housing portions 122a, 122b, respectively, are configured to releasably couple to the distal end of the shaft assembly 216 of the actuating device 212 (see '361 patent for example). A distal end of the shaft assembly 120 includes a pair of upper and lower coupling members 126a, 126b that are configured to couple the shaft assembly 120 to the upper and lower pivot portions 128a, 128b, respectively, of a pivot assembly 130 (see FIG. 21). An articulating link 132 is slidably positioned within the upper and lower housing portions 122a, 122b and is configured to articulate an end effector or tool assembly 114 of the reload 110 relative to a longitudinal axis "C-C" (FIG. 21) defined through the shaft assembly 120.

Figure 23:
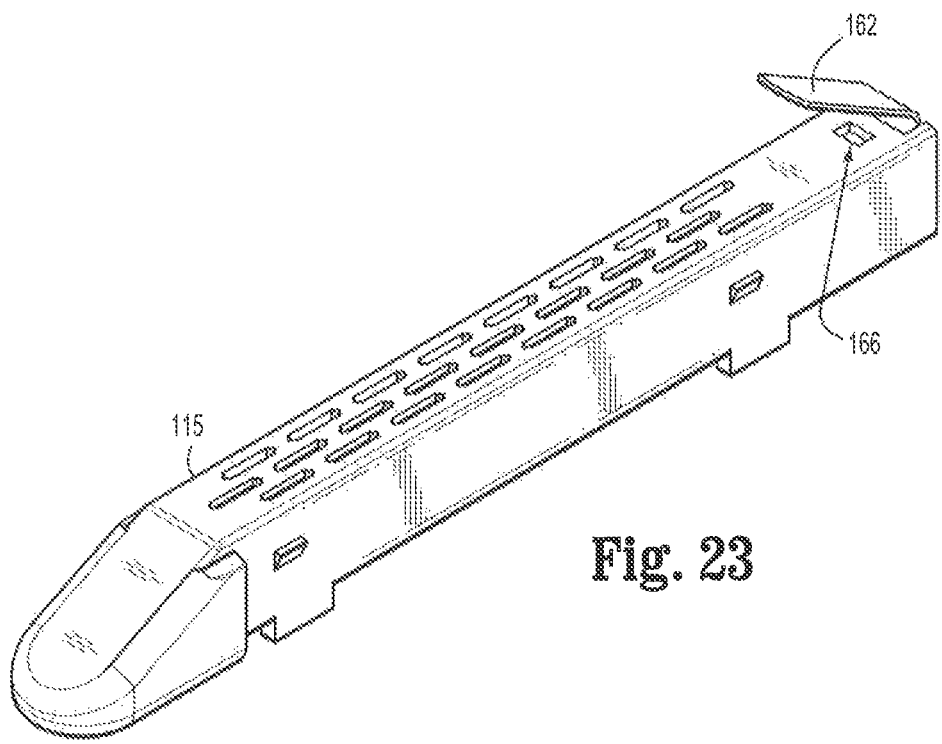
FIG. 23 is a perspective view of a cartridge assembly of the reload shown in FIG. 21.
Figure 24:
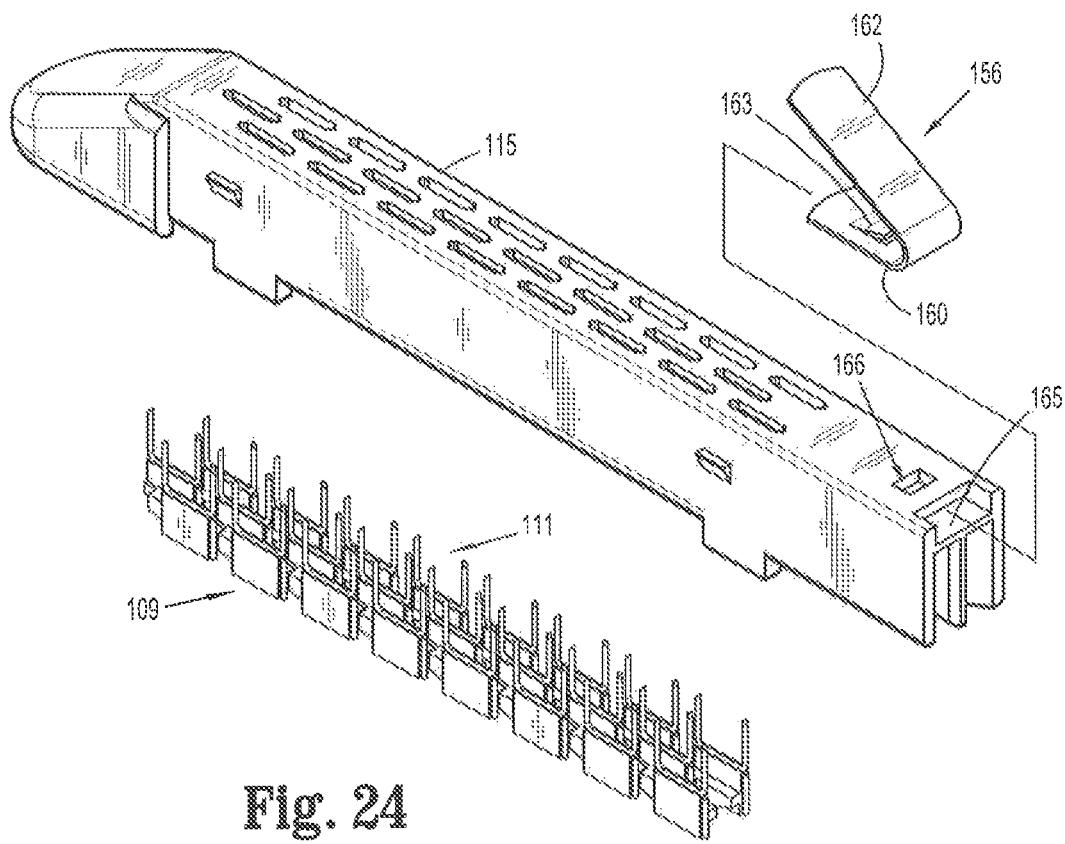
FIG. 24 is an exploded view of the cartridge assembly shown in FIG. 23 with parts separated.

Referring to FIGS. 22-24, the tool assembly 114 includes a first jaw member 113 that supports a cartridge 115 housing a plurality of pushers 109 and fasteners 111 and a second jaw member 117 that supports an anvil 119. The cartridge 115 supports a resilient member 156 which is positioned to bias the cartridge 115 radially away from the anvil 119 towards an unapproximated or spaced configuration. The resilient member 156 includes a base portion 160 (FIG. 24) that couples to a proximal end of the cartridge 115 and an upper portion 162 positioned to contact at least a portion of the anvil 119. The base portion 160 of the resilient member 156 is seated within a corresponding slot 165 defined at the proximal end of the cartridge 115 and includes one or more detents 163 (one detent 163 is shown in the figures) which is received in a corresponding indent 166 disposed on the cartridge 115 adjacent the slot 165 to couple the resilient member 156 to the cartridge 115.

Figure 25:
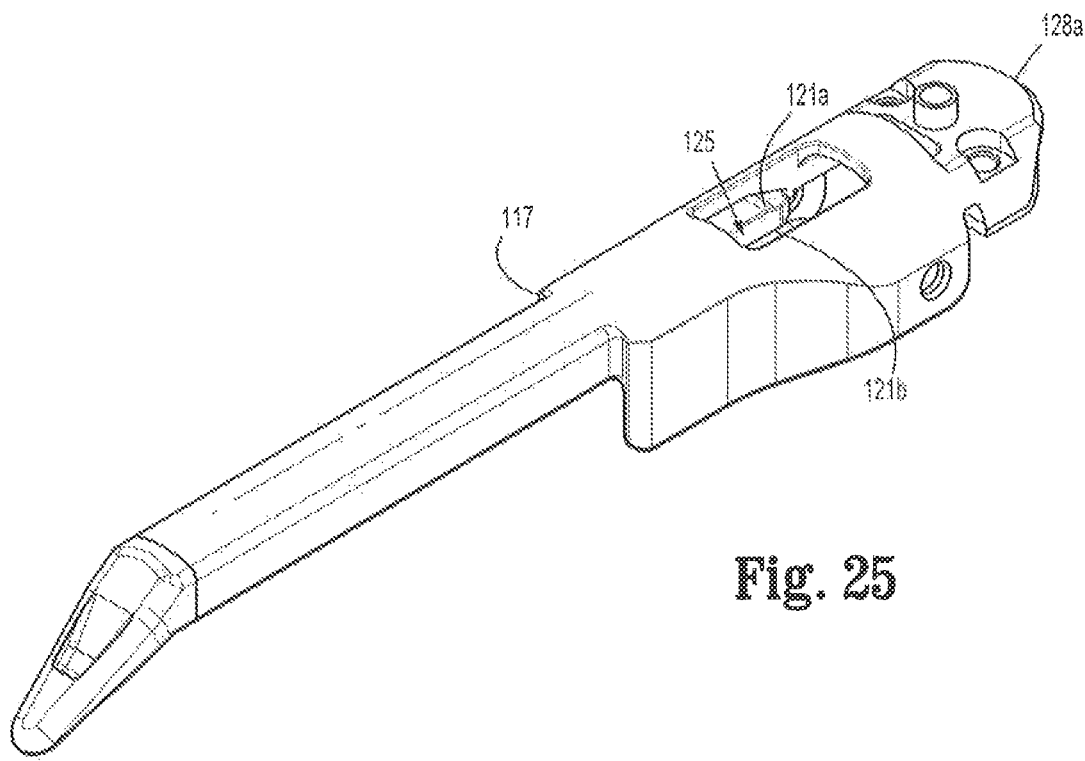
FIG. 25 is a perspective view of a second jaw member of the reload shown in FIG. 21.
Figure 26:
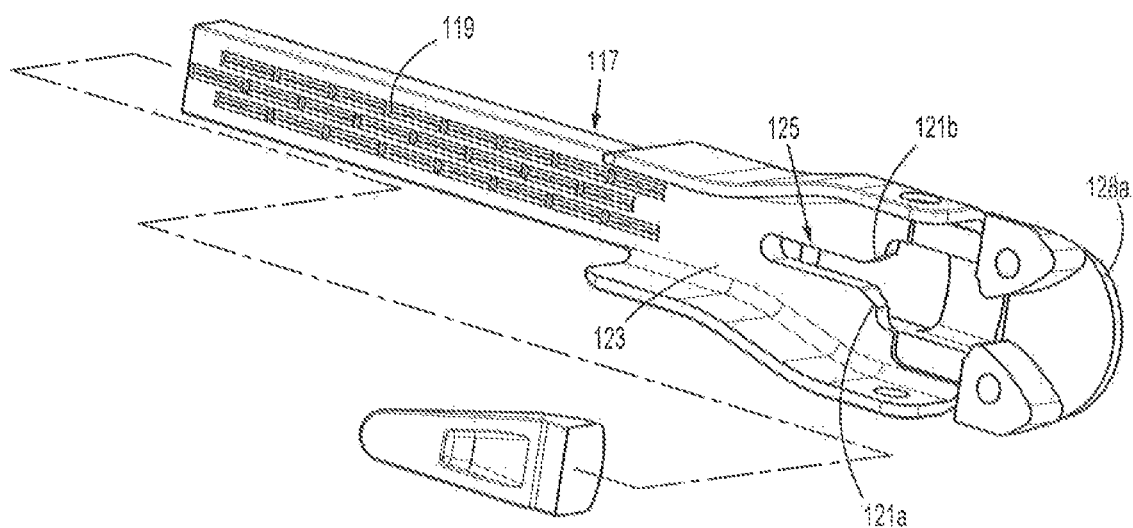
FIG. 26 is an exploded view of the second jaw member shown in FIG. 25 with parts separated.

Referring to FIGS. 25 and 26, the second jaw member 117 includes a pair of upper rails 121a, 121b that extend longitudinally along an interior wall portion 123 of the second jaw member 117. The upper rails 121a, 121b are separated by an elongated slot 125 which extends along the length of the upper rails 121a, 121b. The upper rails 121a, 121b are positioned along the interior wall portion 123 proximal to where the top portion 162 of the resilient member 156 contacts the interior wall portion 123 of the jaw member 117 (see FIG. 35 for example). A dissecting tip 157, such as disclosed in the '123 patent, may be secured to a distal end of the second jaw member 117 to facilitate positioning of the second jaw member 117 in relation to tissue to be stapled.

Figure 27:
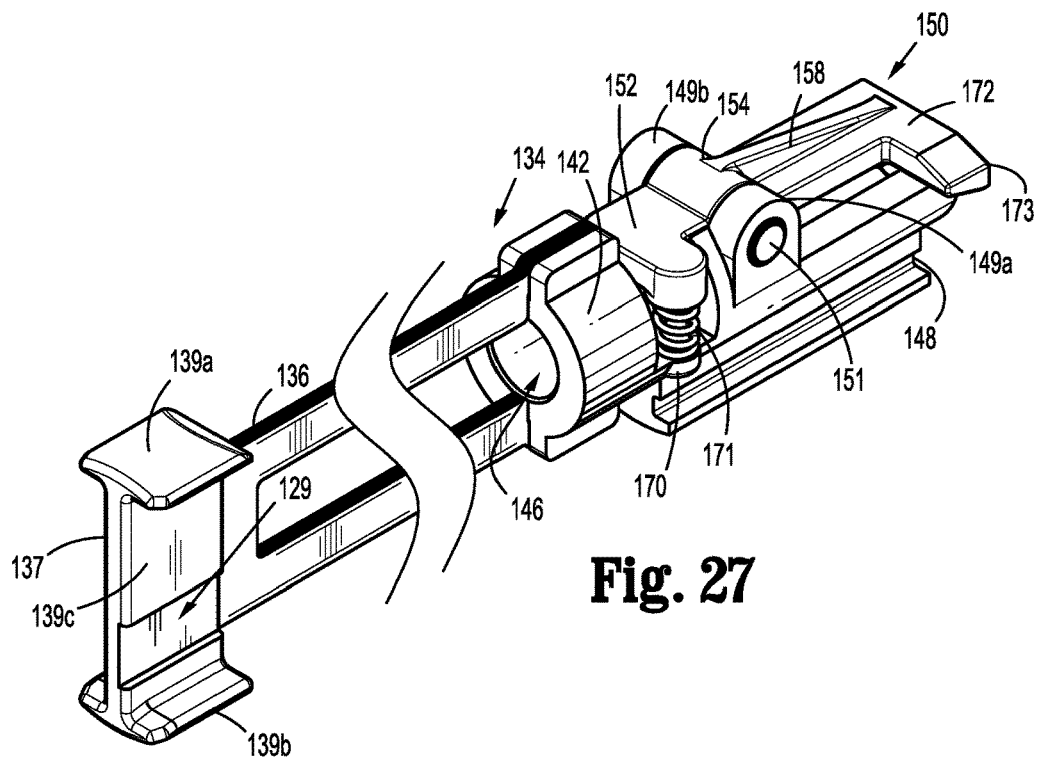
FIG. 27 is a perspective view of a drive beam assembly and latch assembly of the reload shown in FIG. 21.
Figure 28:
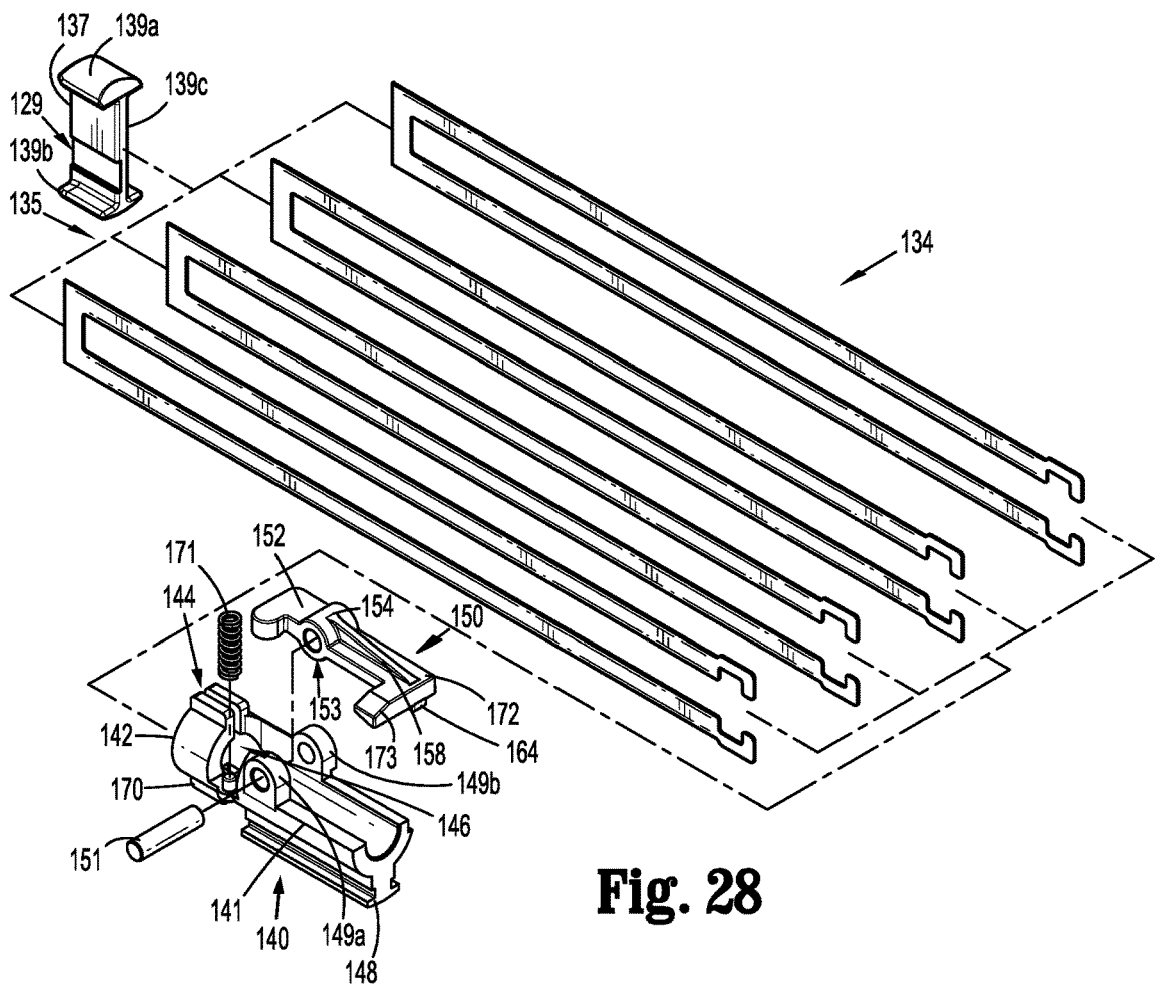
FIG. 28 is an exploded view of the drive beam and latch assembly shown in FIG. 27 with parts separated.

Referring also to FIGS. 27 and 28, the reload 110 (FIG. 21) includes a drive beam assembly 134 formed from a plurality of drive beam portions 135 that are coupled to one another to form a drive beam 136. A working end of the drive beam assembly 134 includes an I-beam 137 which is coupled to the distal end of the drive beam portions 135 and includes upper and lower flanges 139a, 139b respectively connected to each other by a strut 139c. Unlike conventional I-beams, the I-beam 137 does not include a knife or cutting blade at a leading edge of the strut 139c, as the I-beam 137 is not configured to sever stapled tissue. The I-beam 137 is translatable through the tool assembly 114 to approximate the first and second jaw members 113 and 117 and eject fasteners 111 from the cartridge 115 as will be described in further detail below. The upper flange 139a is positioned within the second jaw member 117 (FIG. 26) above the upper rails 121a, 121b. When the drive beam 136 of the drive beam assembly 134 is translated distally within the second jaw member 117, the upper flange 139 slides atop the upper flange 139a to prevent outward movement of the second jaw member 117 in relation to the first jaw member 113. Similarly, the strut 139c of the I-beam is positioned through an elongated slot 127 (see FIG. 31) that is defined through the first jaw member 113 such that the lower flange 139b is slidable along an exterior surface of the first jaw member 113 to prevent outward movement of the first jaw member 113 in relation to the second jaw member 117. A notch 129 is defined through a side wall of the strut 139c, the significance of which is described in greater detail below.

A latch assembly 140 is coupled to a proximal end of the drive beam assembly 134. The latch assembly 140 includes a latch body 141 including a collar 142 defining bottom and top slots 144 (only the top slot 144 is shown). The slots 144 are configured to receive a proximal end of the drive beam 136. A longitudinal aperture 146 of suitable configuration is defined through the collar 142 and is in general alignment with an elongated proximal portion 148 of the latch body 141. The latch body 141 of the latch assembly 140 includes a pair of opposing support members 149a, 149b which support a pivot pin 151. A protrusion 170 extends upwardly from the latch body of the latch assembly 140 adjacent the collar 142 and is configured to support a spring 171.

The latch assembly 140 includes a latch 150 having a generally elongated configuration including a distal portion 152, a medial portion 154 and a proximal portion 158. A transverse aperture 153 extends through the medial portion 154 and is configured to receive the pivot pin 151 for pivotally securing the latch 150 to the latch body 141 of the latch assembly 140. The distal portion 152 of the latch 150 is positioned to contact the spring 171 such that the spring 171 urges a proximal end 172 of the proximal portion 158 of the latch 150 downwardly towards the proximal portion 148 of the latch assembly 140 (as best shown in FIG. 27). A protrusion 164 is provided on a bottom surface and at the proximal end 172 of the proximal portion 158 of the latch assembly 150. A lateral offset extension 173 is also provided at the proximal end 172 of the latch assembly 150 and is configured to move the latch 150 upwardly against the bias of the spring 171, as will be described in greater detail below.

Figure 29:
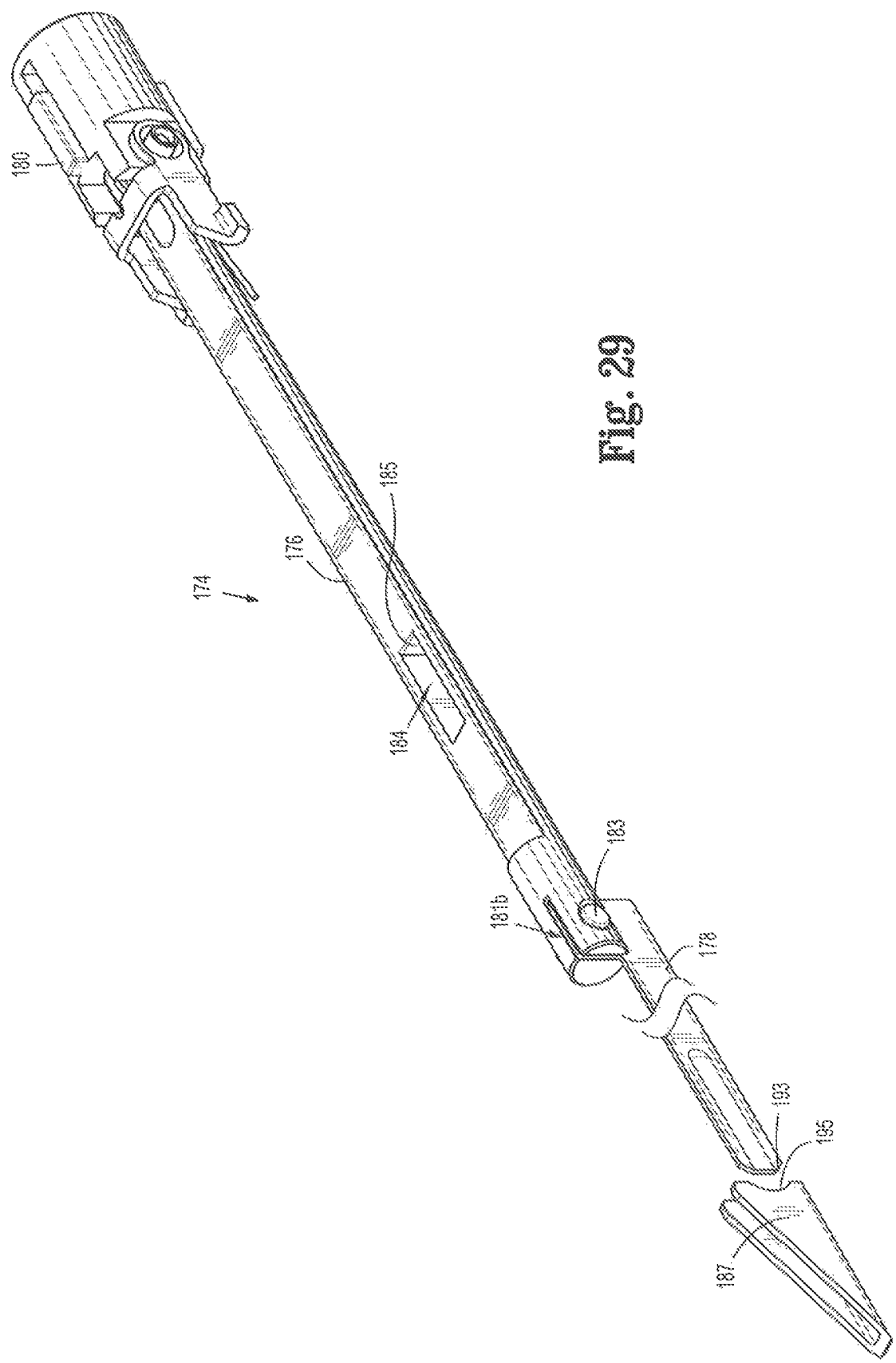
FIG. 29 is a perspective view of a sled pusher assembly of the reload shown in FIG. 21.
Figure 30:
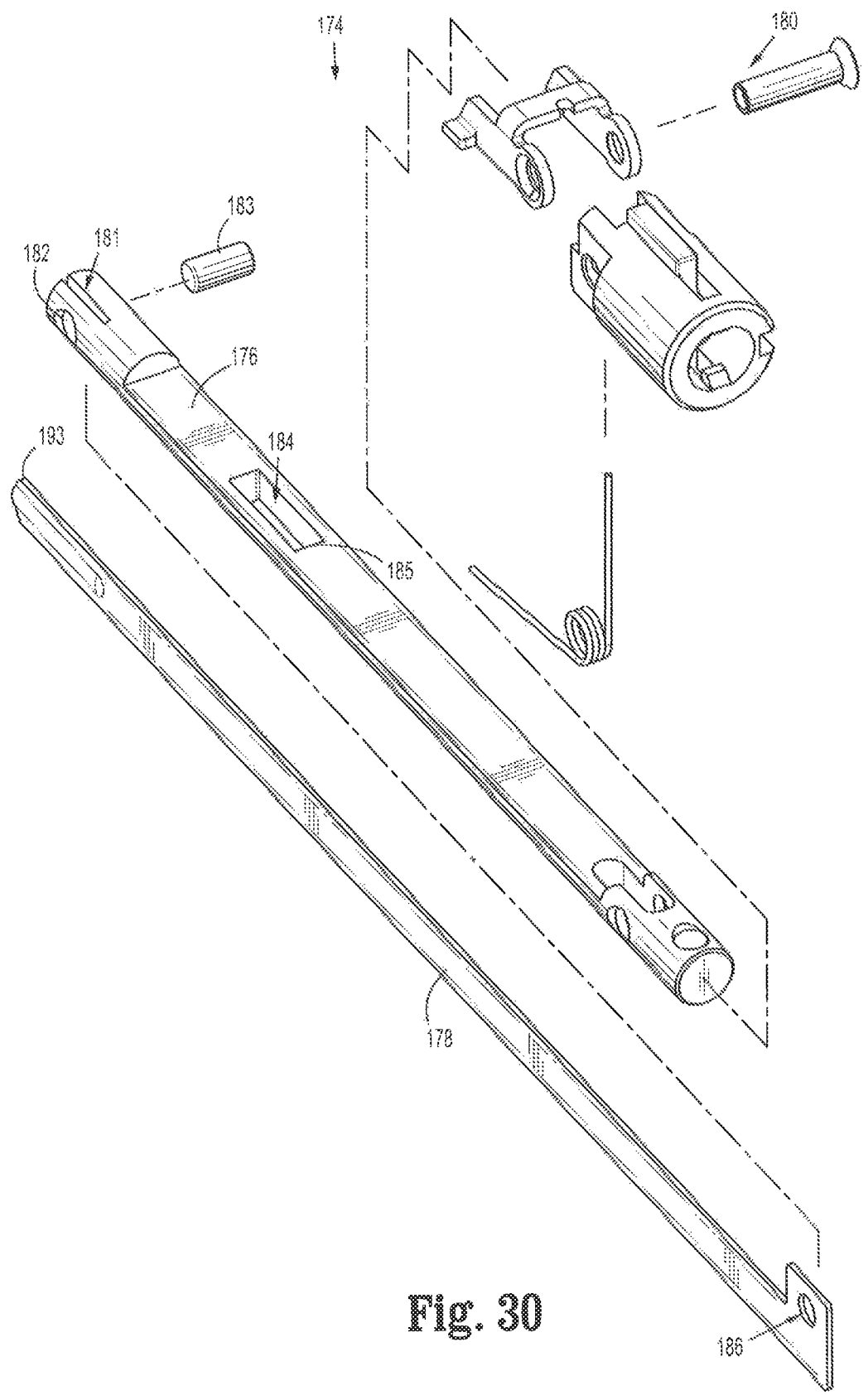
FIG. 30 is an exploded view of the sled pusher assembly shown in FIG. 29 with parts separated.
Figure 31:
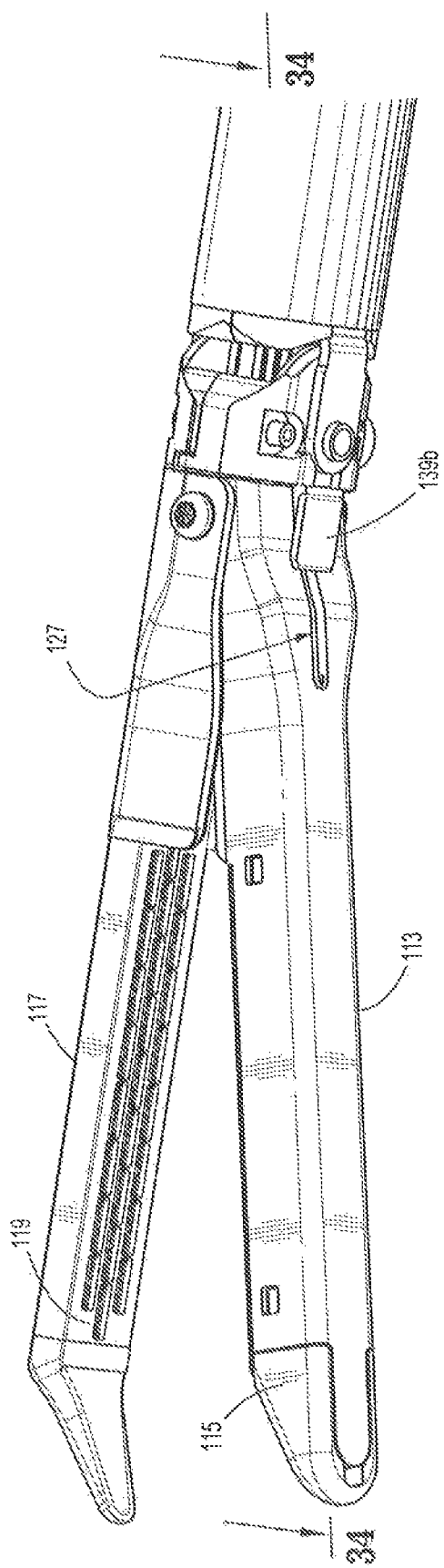
FIG. 31 is a partial, perspective view of the reload shown FIG. 21 with a distal end of the reload shown in an unclamped configuration.

Referring to FIGS. 29 and 30, a sled pusher assembly 174 is illustrated. The sled pusher assembly 174 includes an elongated support member 176 which has a distal end that engages a sled pusher 178 and a proximal end which supports a coupling assembly 180. The distal end of the support member 176 defines a slit 181 and a pair of apertures 182 (only one aperture 182 is shown). The apertures 182 extend through the slit 181 and receive a pin 183, rivet or the like. The slit 181 is configured to receive a proximal end of the sled pusher 178. The pin 183 extends through an aperture 186 defined through the proximal end of the sled pusher 178 to secure the sled pusher 178 to the support member 176. As can be appreciated other coupling methods could also be utilized to couple the sled pusher 178 to the support member 176.

Figure 33:
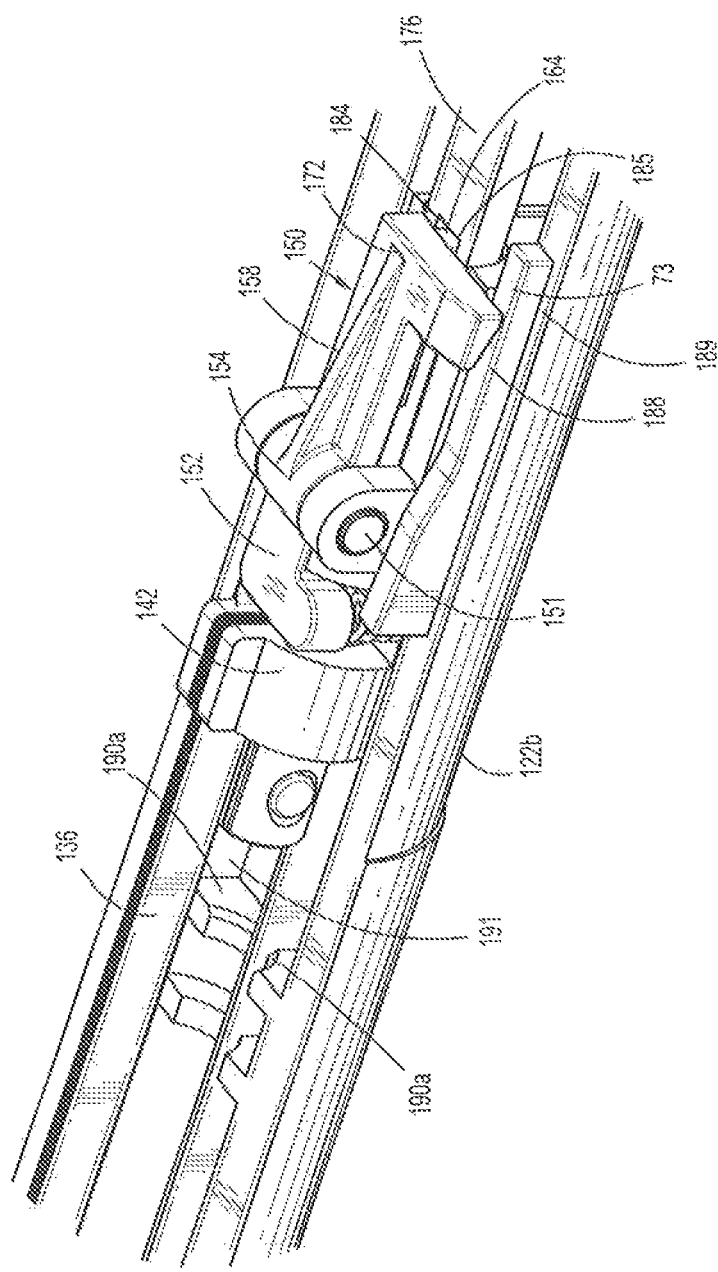
FIG. 33 is the indicated area of detail shown in FIG. 32.

An aperture 184 is provided on the support member 176. The aperture 184 is configured to receive the protrusion 164 of the latch 150 such that the protrusion 164 contacts a proximal wall portion 185 defining the aperture 184 (FIG. 33). In accordance with the instant disclosure, when the protrusion 164 is in contact with the proximal wall portion 185, the sled pusher assembly 174 and the and the drive beam assembly 134 are releasably coupled to one another such that movement of sled pusher assembly 174 effects corresponding movement of the drive beam assembly 134 to effect movement of the first jaw member 113 towards the second jaw member 117.

Figure 32:
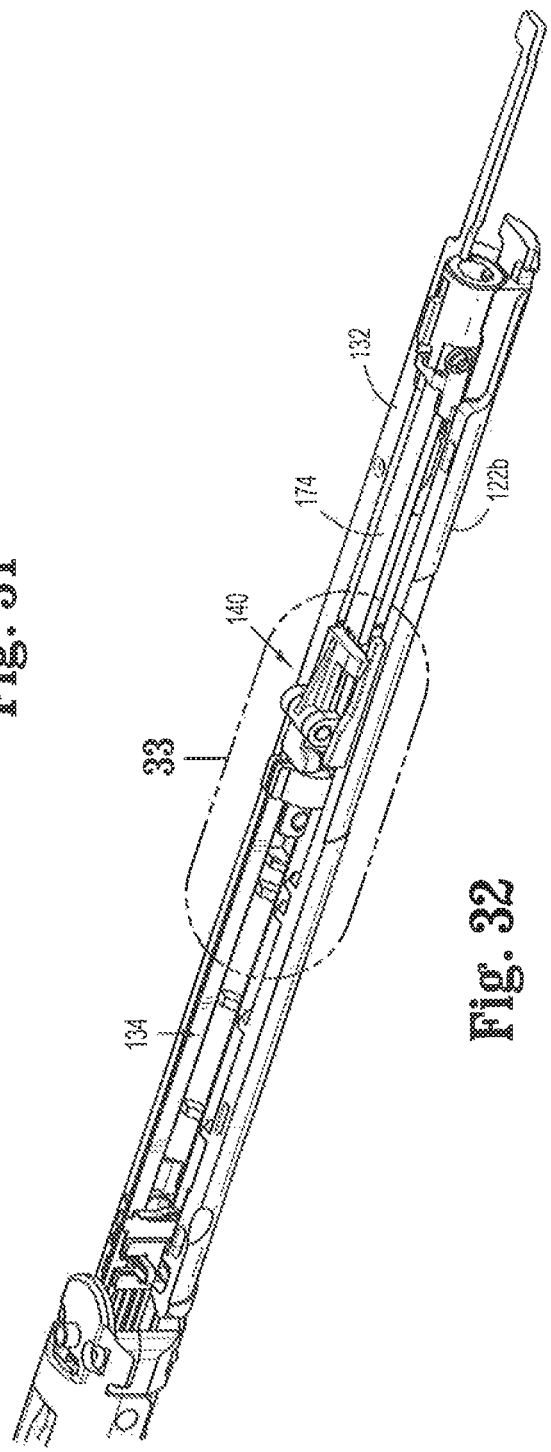
FIG. 32 is a partial, perspective view of the reload shown in FIG. 21 with parts removed illustrating the drive beam assembly and latch assembly when the distal end of the reload is in the unclamped configuration shown in FIG. 31.

Referring also to FIGS. 32 and 33, the lower housing portion 122b supports the drive assembly 134 including the latch assembly 140 and the sled pusher assembly 174. The lower housing portion 122b is configured to disengage the latch 150 of the latch assembly 140 from the sled pusher assembly 174 to allow further distal translation of the sled pusher assembly 174 independently of the drive beam assembly 134. Specifically, a ramp portion 188 is provided along a top wall 189 of the lower housing portion 122b. The ramp portion 188 is configured to contact the lateral offset extension 173 of the latch 150 to pivot the latch 150 about pivot member 151 to raise the protrusion 164 of the latch 150 out from engagement with the aperture 184 of the support member 176 of the sled pusher assembly 174 when the drive beam assembly 134 and sled pusher assembly 174 are translated distally to approximate the jaw members 113 and 117.

A pair of stops 190a are provided along an interior wall portion 191 of the lower housing portion 122b. Stops 190a are positioned to contact a lower portion of the collar 142 of the latch assembly 140 to prevent further distal translation of the drive beam assembly 134 after the collar 142 engages the stops 190a. In the illustrated embodiment, a corresponding pair of stops 190b (FIG. 39) is provided on the upper housing portion 122a and is configured to contact an upper portion of the collar 142 of the latch assembly 140 to prevent further distal translation of the drive beam assembly 134 after the collar 142 engages the stops 190a.

Figure 34:
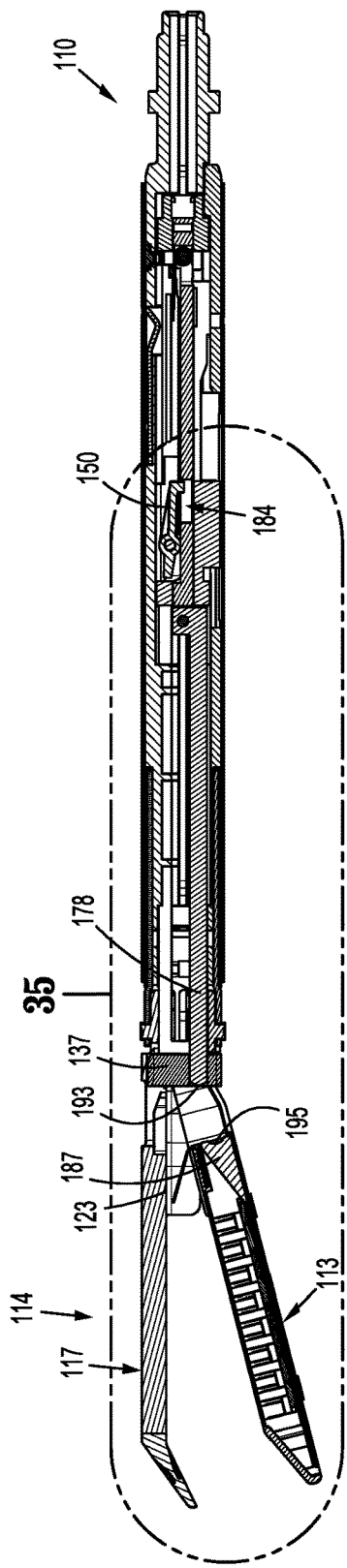
FIG. 34 is a cross sectional view taken along section line 34-34 in FIG. 31.
Figure 35:
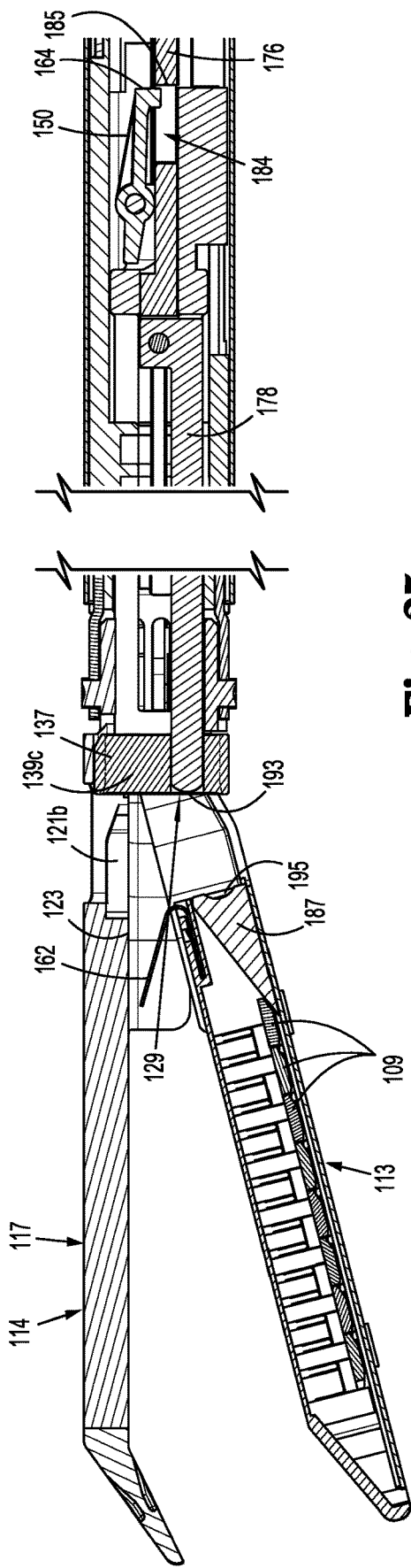
FIG. 35 is the indicated area of detail shown in FIG. 34.

FIGS. 34-44 illustrate the operation of the reload 110. Referring to FIGS. 33-35, prior to positioning tissue between the first and second jaw members 113, 117, the tool assembly 114 is urged to the spaced or unapproximated position by the resilient member 156 which contacts the interior wall 123 of the second jaw member 117 (FIGS. 34 and 35). In the spaced position, the protrusion 164 of the latch 150 is in contact with the proximal wall portion 185 defining the aperture 184 in the support member 176 to releasably couple the sled pusher assembly 174 to the drive beam assembly 134 such that distal translation of the sled pusher assembly 174 effects corresponding movement of the drive beam assembly 134.

In the spaced position of the jaw members 113 and 117, the distal end of the support member 176 is positioned through the longitudinal aperture 146 of the collar 142 of the latch assembly 140 and the sled pusher 178 is positioned within the notch 129 of strut 139c of the I-beam 137 to align a distal end 193 of the sled pusher 178 with a sled 187 that is provided in the cartridge 115 (FIG. 35). The distal end 193 of the sled pusher 178 is configured to engage a proximal end 195 of the sled 187 when the sled pusher 178 is translated distally into the cartridge 115. In the illustrated embodiment, the distal end 193 of the sled pusher 178 and the proximal end 195 of the sled 187 include complementary configurations, e.g., spherical configurations, to facilitate engagement therebetween. The sled 187 is configured to sequentially contact the plurality of pushers 109 to eject the plurality of fasteners 111 from the cartridge 115 as is known in the art.

Figure 36:
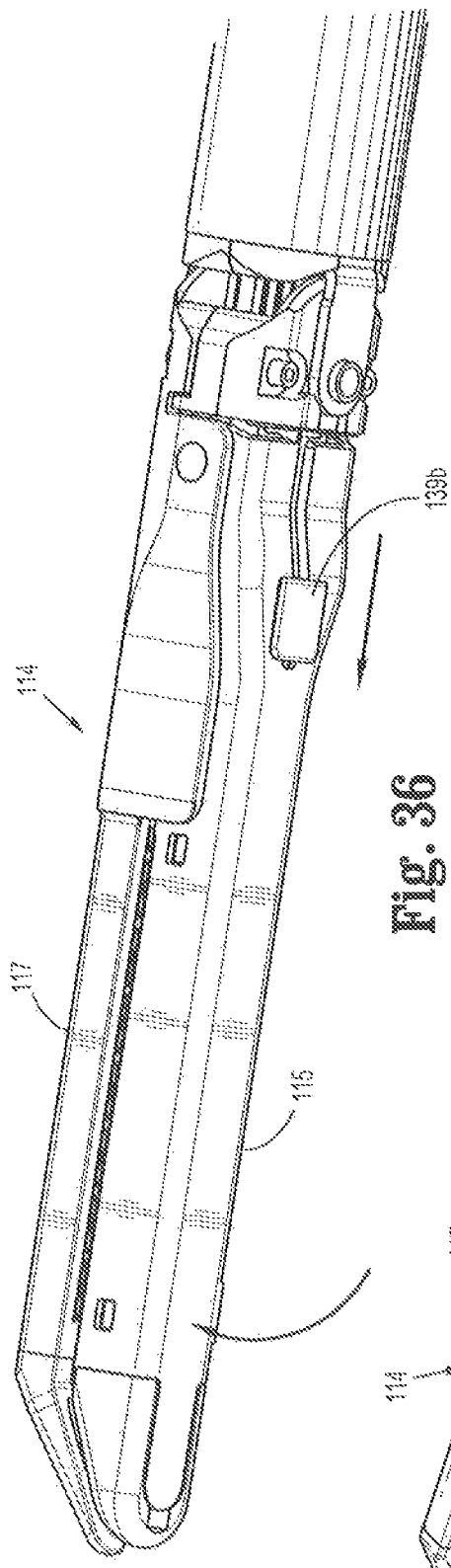
FIG. 36 is a partial, perspective view of the reload shown in FIG. 21 with a distal end of the reload shown in a clamped configuration.
Figure 37:
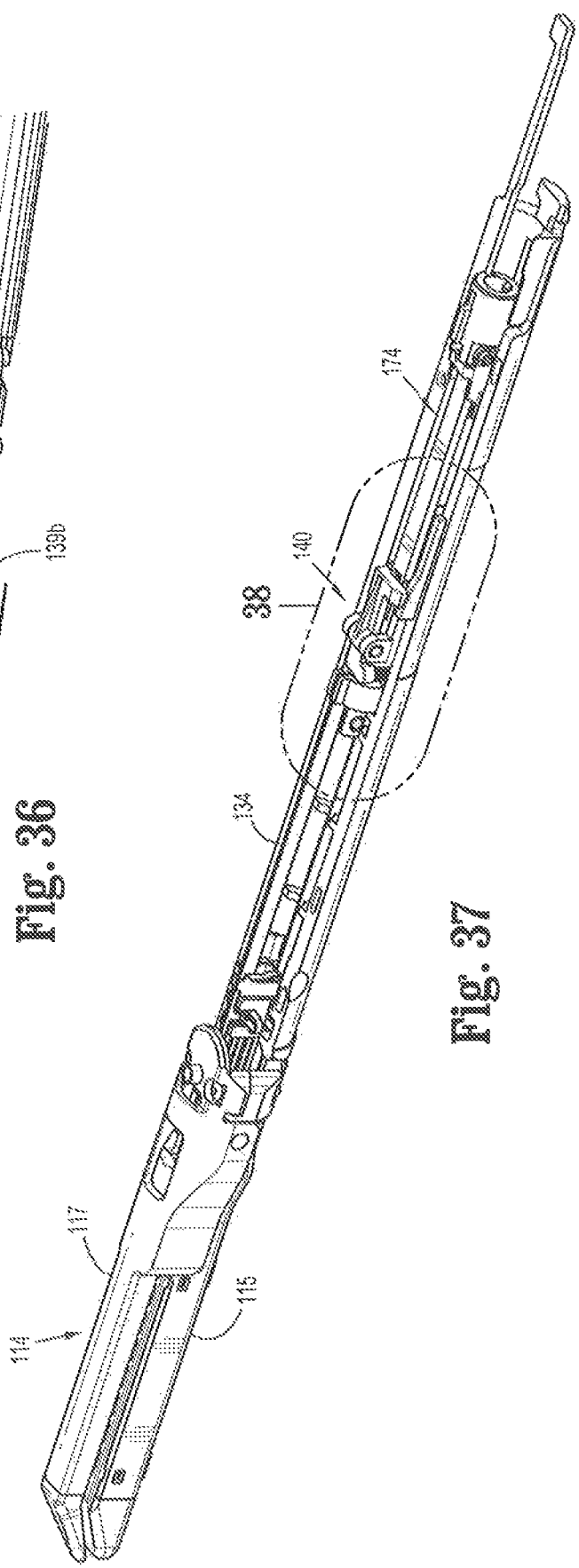
FIG. 37 is a partial, perspective view of the reload shown in FIG. 21 with parts removed illustrating the drive beam assembly and latch assembly when the distal end of the reload is in the clamped configuration shown in FIG. 36.

Referring to FIGS. 36-41, when the surgical actuating device 12 (FIG. 1B) is actuated to advance the sled pusher assembly 174, the drive assembly 134 which is releasably coupled to the sled pusher assembly 174 is advanced distally to move the I-beam 137 distally in relation to the tool assembly 114. As the I-beam is moved distally, the upper and lower flanges 139a, 139b of the I-beam 137 engage the first and second jaw members 113, 117, respectively, such that the first jaw member 113 is moved towards the second jaw member 117 to the clamped or approximated position of the tool assembly 114 to clamp tissue (FIG. 36). As noted above, the drive assembly 134 and the sled pusher assembly 174 move in unison as a result of the protrusion 164 being in contact with the proximal wall portion 185 defining the aperture 184 of the support member 176.

As the drive assembly 134 is moved distally to move the jaw members 113 and 117 to the clamped or approximated position, the lateral offset 173 (FIG. 38) of the latch 150 slides up along the ramp 188 of the lower housing portion 122b and raises the latch 150 to disengage the protrusion 164 of the latch 140 from engagement with the proximal wall portion 185 of the support member 176. In the approximated position of the jaw members 113 and 117, the sled pusher assembly 174 is uncoupled from the drive assembly 134 and the distal end 193 of the sled pusher 178 is positioned in engagement with the proximal end 195 of the sled 187 (as best shown in FIG. 41).

In the approximated position, the collar 142 is in contact with the stops 190a in the lower housing portion 122b (FIGS. 38 and 42) and the upper portion of the collar 142 is in contact with the stops 190b in the upper housing portion 122a. Engagement between stops 190a and collar 142 prevents further distal movement of the drive beam assembly 134.

Figure 42:
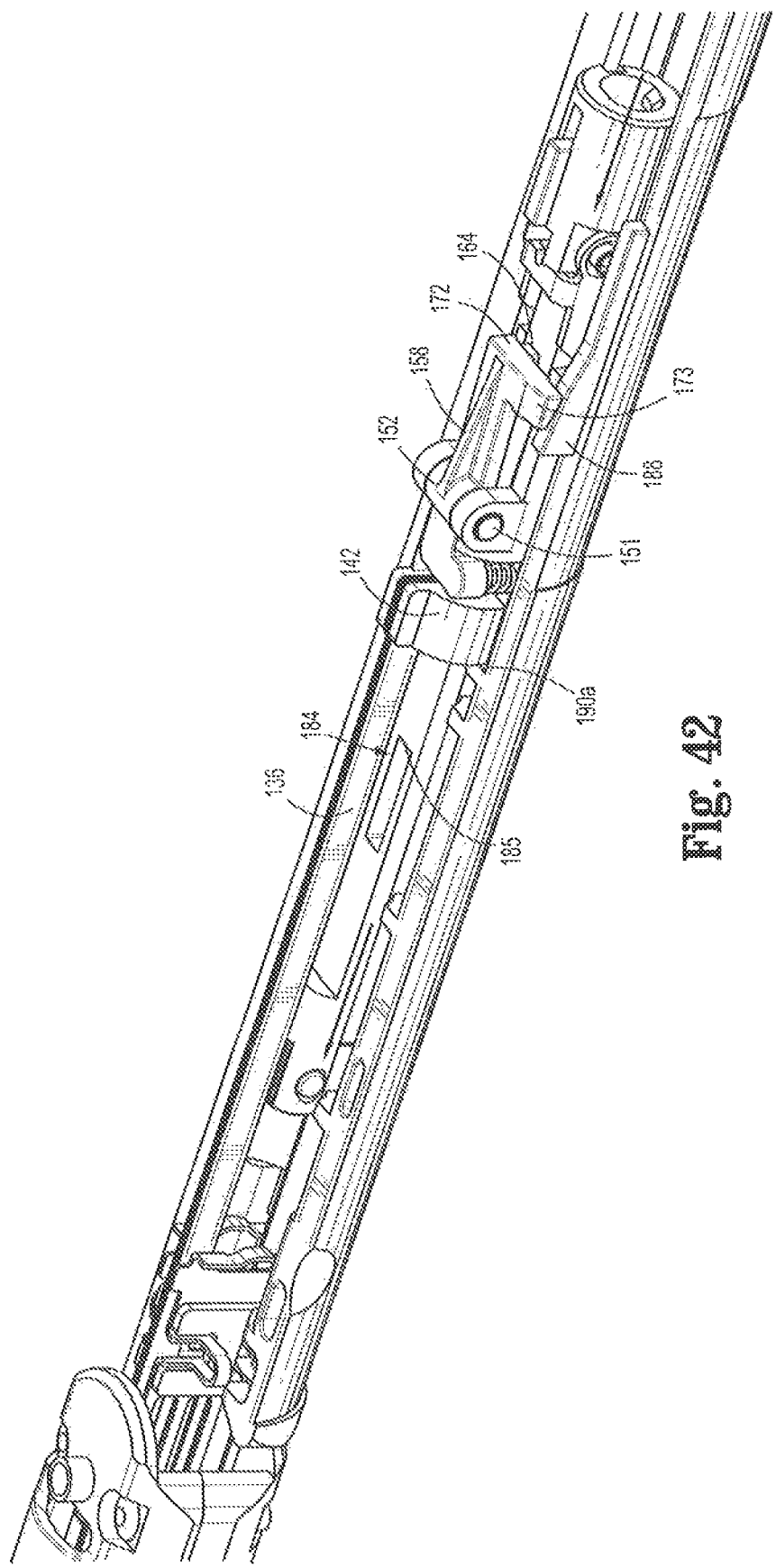
FIG. 42 is a partial, perspective view of the reload shown in FIG. 21 with parts removed illustrating the sled pusher assembly shown in FIG. 29 as the sled pusher assembly is being fired.
Figure 43:
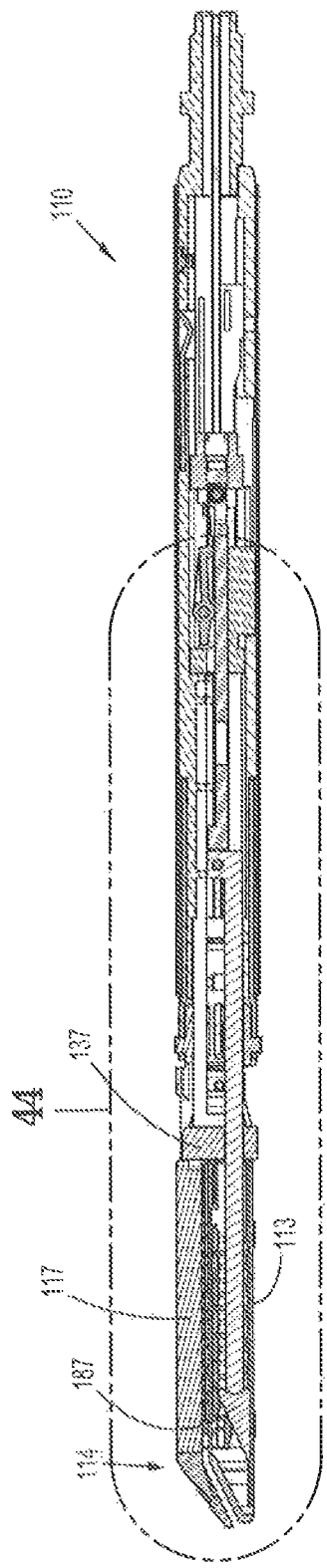
FIG. 43 is a cross sectional view of the reload shown in FIG. 21 with the reload shown in the clamped configuration and the sled pusher assembly being fired.
Figure 44:
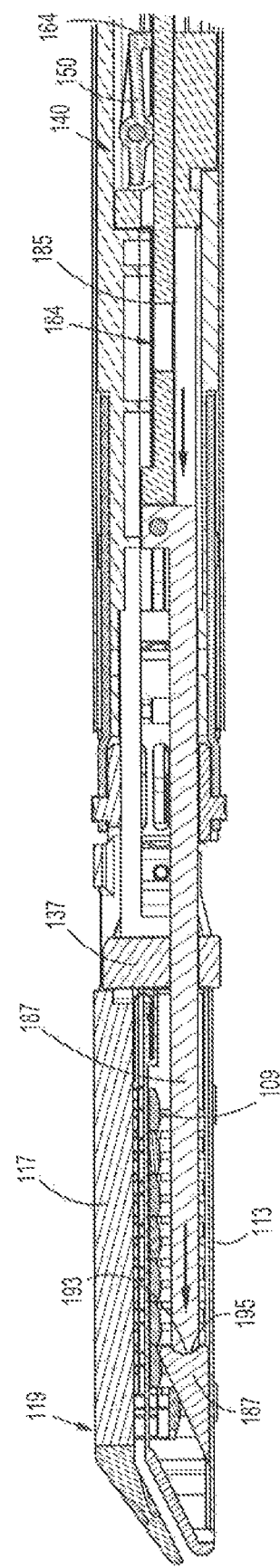
FIG. 44 is the indicated area of detail shown in FIG. 43.

Referring to FIGS. 42-44, after the sled pusher assembly 174 is uncoupled from the drive assembly 134, further actuation of the actuating device 12 effects independent movement of the sled pusher assembly 174 through the aperture 146 of the collar 142 such that the distal end 193 of the sled pusher 178 moves distally in relation to the I-beam 137 of the drive assembly 134 to advance the sled 187 through the cartridge 115 into sequential engagement with the pushers 109 to eject the plurality of fasteners 111 from the cartridge 115 (FIGS. 43 and 44).

While the reloads 10, 110 have been described herein as being configured for use with the stapler 212, it is within the purview of the present disclosure that the operative components of the reloads 10, 110 may be incorporated into a stapler with a tool assembly fixedly attached thereto.

The stapler 212 with either of the reloads 10, 110 attached thereto can be utilized to staple various tissue structures. For example, during a transplant procedure, where blood flow through vascular structure adjacent a transplant site needs to be controlled or inhibited, the stapler 212 can be utilized to staple (i.e., occlude) this vascular structure, thereby controlling and/or inhibiting blood flow through the vascular structure. It is contemplated that the stapler 212 with either of the reloads 10, 110 attached thereto can be utilized to staple other types of tissue structures and/or can be utilized in conjunction with other surgical procedures.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical stapling apparatus, comprising:
   a handle assembly;
   an elongated shaft extending from the handle assembly; and
   a reload coupled to the elongated shaft, the reload including:
      a tool assembly including a first jaw member pivotably coupled to a second jaw member, the first jaw member supporting a cartridge including a sled and a plurality of fasteners, and the second jaw member supporting an anvil;
      a sled pusher assembly configured to contact the sled of the cartridge;
      a drive beam assembly configured to move the first and second jaw members from a spaced position to an approximated position; and
      a latch assembly including a latch body coupled to the drive beam assembly and a latch pivotally secured to the latch body, the latch assembly releasably coupled to the sled pusher assembly,
      wherein when the latch assembly is coupled to the sled pusher assembly, distal translation of the sled pusher assembly effects distal translation of the drive beam assembly to move the first and second jaw members towards the approximated position and, when the latch assembly is uncoupled from the sled pusher assembly, the sled pusher assembly translates distally independently of the drive beam assembly and engages the sled of the cartridge to eject the plurality of fasteners from the cartridge.

2. The surgical stapling apparatus of claim 1, wherein the cartridge of the first jaw member supports a resilient member for biasing the first and second jaw members towards the spaced position.

3. The surgical stapling apparatus of claim 1, wherein the cartridge of the first jaw member includes three rows of fastener retention slots.

4. The surgical stapling apparatus of claim 1, wherein the anvil of the second jaw member includes a dissecting tip.

5. The surgical stapling apparatus of claim 1, wherein the drive beam assembly includes a drive beam and an I-beam coupled to a distal end of the drive beam, the I-beam translatable through the tool assembly to approximate the first and second jaw members.

6. The surgical stapling apparatus of claim 5, wherein the I-beam of the drive beam assembly has a blunt leading edge.

7. The surgical stapling apparatus of claim 5, wherein the I-beam includes a notch defined through a side wall thereof, and the sled pusher assembly includes a sled pusher positioned within the notch of the I-beam to align the sled pusher with the sled of the cartridge.

8. The surgical stapling apparatus of claim 1, wherein the latch body of the latch assembly includes a longitudinal aperture, and the sled pusher assembly includes an elongated support member positioned through the longitudinal aperture.

9. The surgical stapling apparatus of claim 8, wherein the elongated support member of the sled pusher assembly includes an aperture configured to receive a protrusion of the latch of the latch assembly.

10. The surgical stapling apparatus of claim 9, wherein the latch assembly includes a spring configured to bias the protrusion of the latch into the aperture defined in the elongated support member of the sled pusher assembly.

11. The surgical stapling apparatus of claim 9, wherein the latch assembly includes a lateral offset extension configured to move the protrusion of the latch out from engagement with the aperture defined in the elongated support member of the sled pusher assembly.

12. The surgical stapling apparatus of claim 11, wherein the reload further includes an outer tube housing a shaft assembly configured to couple the reload to the elongated shaft.

13. The surgical stapling apparatus of claim 12, wherein the shaft assembly includes a ramp portion configured to contact the lateral offset extension of the latch assembly to pivot the latch when the drive beam assembly and the sled pusher assembly are translated distally to approximate the first and second jaw members.

14. The surgical stapling apparatus of claim 12, wherein the shaft assembly includes a stop positioned to contact the latch body of the latch assembly during distal translation of the drive beam assembly to prevent further distal translation of the drive beam assembly.

15. A reload for use with a surgical stapling apparatus, the reload comprising:
- an outer tube housing a shaft assembly;
- a tool assembly extending distally from the outer tube, the tool assembly including a first jaw member pivotably coupled to a second jaw member, the first jaw member supporting a cartridge including a sled and a plurality of fasteners, and the second jaw member supporting an anvil;
- a sled pusher assembly supported within the shaft assembly and configured to contact the sled of the cartridge;
- a drive beam assembly supported within the shaft assembly and configured to move the first and second jaw members of the tool assembly from a spaced position to an approximated position; and
- a latch assembly including a latch body coupled to the drive beam assembly and a latch pivotally secured to the latch body, the latch assembly releasably coupled to the sled pusher assembly,
- wherein when the latch assembly is coupled to the sled pusher assembly, distal translation of the sled pusher assembly effects distal translation of the drive beam assembly to move the first and second jaw members towards the approximated position and, when the latch assembly is uncoupled from the sled pusher assembly, the sled pusher assembly translates distally independently of the drive beam assembly and engages the sled of the cartridge to eject the plurality of fasteners from the cartridge.

16. A surgical stapling apparatus, comprising:
- a handle assembly;
- an elongated shaft extending from the handle assembly; and
- a reload coupled to the elongated shaft, the reload including:
  - a tool assembly including a first jaw member pivotably coupled to a second jaw member, the first jaw member supporting a cartridge including a sled and a plurality of fasteners, and the second jaw member supporting an anvil;
  - a sled pusher assembly including a sled pusher configured to contact the sled of the cartridge;
  - a drive beam assembly configured to move the first and second jaw members from a spaced position to an approximated position, the drive beam assembly including a drive beam and an I-beam coupled to a distal end of the drive beam, the I-beam translatable through the tool assembly to approximate the first and second jaw members, the I-beam including a notch defined through a side wall thereof and the sled pusher of the sled pusher assembly positioned within the notch of the I-beam to align the sled pusher with the sled of the cartridge; and
  - a latch assembly coupled to the drive beam assembly and releasably coupled to the sled pusher assembly,
- wherein when the latch assembly is coupled to the sled pusher assembly, distal translation of the sled pusher assembly effects distal translation of the drive beam assembly to move the first and second jaw members towards the approximated position and, when the latch assembly is uncoupled from the sled pusher assembly, the sled pusher assembly translates distally independently of the drive beam assembly and engages the sled of the cartridge to eject the plurality of fasteners from the cartridge.

* * * * *